(12) United States Patent
Davidson et al.

US011690933B2

(10) Patent No.: US 11,690,933 B2
(45) Date of Patent: Jul. 4, 2023

(54) ABSORBENT ALIPHATIC POLYURETHANE FOAM PRODUCT

(71) Applicant: SENTIENT FOAMS LIMITED, Hereford (GB)

(72) Inventors: Roderick Davidson, Hereford (GB); Chaminda Koralalage, Hereford (GB)

(73) Assignee: SENTIENT FOAMS LIMITED, Hereford (GB)

( * ) Notice: Subject to any disclaimer, the term of this patent is extended or adjusted under 35 U.S.C. 154(b) by 0 days.

(21) Appl. No.: 16/308,756

(22) PCT Filed: Jun. 9, 2017

(86) PCT No.: PCT/GB2017/051694
§ 371 (c)(1),
(2) Date: Dec. 10, 2018

(87) PCT Pub. No.: WO2017/212292
PCT Pub. Date: Dec. 14, 2017

(65) Prior Publication Data
US 2019/0142992 A1 May 16, 2019

(30) Foreign Application Priority Data
Jun. 10, 2016 (GB) ..................... 1610184

(51) Int. Cl.
*A61L 15/26* (2006.01)
*C08J 9/36* (2006.01)
*A61L 15/42* (2006.01)
*C08G 18/10* (2006.01)
*C08G 18/73* (2006.01)
*B32B 3/14* (2006.01)
*B32B 29/00* (2006.01)
*A61F 13/00* (2006.01)
*B29C 44/56* (2006.01)
*B32B 5/18* (2006.01)
(Continued)

(52) U.S. Cl.
CPC ............ *A61L 15/26* (2013.01); *A61F 13/00* (2013.01); *A61F 13/141* (2013.01); *A61K 9/122* (2013.01); *A61K 31/155* (2013.01); *A61K 33/20* (2013.01); *A61L 15/425* (2013.01); *B01J 20/262* (2013.01); *B01J 20/28011* (2013.01); *B01J 20/28045* (2013.01); *B01J 20/3035* (2013.01); *B01J 20/3064* (2013.01); *B01J 20/3085* (2013.01); *B29C 44/569* (2013.01); *B29C 44/5627* (2013.01); *B32B 3/14* (2013.01); *B32B 5/022* (2013.01); *B32B 5/18* (2013.01); *B32B 5/245* (2013.01); *B32B 5/32* (2013.01); *B32B 27/065* (2013.01); *B32B 29/007* (2013.01); *C08G 18/10* (2013.01); *C08G 18/4829* (2013.01); *C08G 18/73* (2013.01); *C08J 9/122* (2013.01);

*C08J 9/36* (2013.01); *B29C 59/04* (2013.01); *B29K 2075/00* (2013.01); *B29K 2105/0005* (2013.01); *B29K 2105/24* (2013.01); *B29K 2995/0063* (2013.01); *B29K 2995/0068* (2013.01); *B29K 2995/0094* (2013.01); *B29L 2009/00* (2013.01); *B32B 2255/12* (2013.01); *B32B 2255/26* (2013.01); *B32B 2262/0276* (2013.01); *B32B 2266/0278* (2013.01); *B32B 2307/306* (2013.01); *B32B 2307/54* (2013.01); *B32B 2307/72* (2013.01); *B32B 2307/726* (2013.01); *B32B 2307/728* (2013.01); *B32B 2307/732* (2013.01); *B32B 2555/00* (2013.01); *B32B 2555/02* (2013.01); *C08G 2101/00* (2013.01); *C08G 2110/0025* (2021.01); *C08G 2110/0058* (2021.01); *C08G 2110/0066* (2021.01); *C08G 2110/0083* (2021.01); *C08J 2203/06* (2013.01); *C08J 2205/10* (2013.01); *C08J 2207/12* (2013.01); *C08J 2375/04* (2013.01); *C08J 2375/08* (2013.01)

(58) Field of Classification Search
CPC ................ A61F 13/00; A61F 13/00059; A61F 2013/00617
See application file for complete search history.

(56) References Cited

U.S. PATENT DOCUMENTS 2,649,088 A 8/1953 Sigg
4,073,991 A 2/1978 Focht
(Continued)

FOREIGN PATENT DOCUMENTS

BE 829878 A 10/1975
CN 102131528 A 7/2011
(Continued)

OTHER PUBLICATIONS

En Iso 527-2 "Plastics—Determination of tensile properties—Part 2 Test conditions for moulding and extrusion plastics", (2012).
(Continued)

*Primary Examiner* — Andrew S Rosenthal
*Assistant Examiner* — Lyndsey M Beckhardt
(74) *Attorney, Agent, or Firm* — Nixon Peabody LLP; David S. Resnick; Nicole D. Kling

(57) ABSTRACT

The present invention relates to foam. In particular, the present invention relates to profiled foams and processes for profiling absorbent foam products. More particularly, the present invention relates to processes for producing a profiled absorbent polyurethane foam product, comprising the steps of foaming, curing, profiling and drying, wherein profiling occurs before drying; and absorbent aliphatic polyurethane foam products having at least one profiled surface.

16 Claims, 18 Drawing Sheets

(51) Int. Cl.
| | |
|---|---|
| *B32B 5/24* | (2006.01) |
| *B32B 5/02* | (2006.01) |
| *A61F 13/14* | (2006.01) |
| *B32B 27/06* | (2006.01) |
| *B32B 5/32* | (2006.01) |
| *A61K 9/12* | (2006.01) |
| *A61K 31/155* | (2006.01) |
| *A61K 33/20* | (2006.01) |
| *B01J 20/26* | (2006.01) |
| *B01J 20/28* | (2006.01) |
| *B01J 20/30* | (2006.01) |
| *C08G 18/48* | (2006.01) |
| *C08J 9/12* | (2006.01) |
| *B29K 105/00* | (2006.01) |
| *B29C 59/04* | (2006.01) |
| *B29K 75/00* | (2006.01) |
| *B29K 105/24* | (2006.01) |
| *B29L 9/00* | (2006.01) |
| *C08G 101/00* | (2006.01) |

(56) References Cited

U.S. PATENT DOCUMENTS

| | | | |
|---|---|---|---|
| 4,343,866 | A | 8/1982 | Oser et al. |
| 4,740,258 | A | 4/1988 | Breitscheidel |
| 4,867,748 | A | 9/1989 | Samuelsen |
| 5,074,944 | A | 12/1991 | Trenka |
| 6,616,642 | B1 | 9/2003 | Jensen et al. |
| 7,396,975 | B2 | 7/2008 | Sigurjonsson et al. |
| 7,488,864 | B2 | 2/2009 | Sigurjonsson et al. |
| 7,696,400 | B2 | 4/2010 | Sigurjonsson et al. |
| 7,745,682 | B2 | 6/2010 | Sigurjonsson et al. |
| 8,080,703 | B2 | 12/2011 | Marcussen |
| 2002/0160037 | A1 | 10/2002 | Ahrens et al. |
| 2003/0093050 | A1 | 5/2003 | Baker |
| 2003/0097103 | A1* | 5/2003 | Horney ............... A61F 13/532 604/369 |
| 2004/0058129 | A1* | 3/2004 | Bouic ................ B05B 12/24 428/156 |
| 2007/0077220 | A1 | 4/2007 | Ramirez et al. |
| 2009/0018480 | A1 | 1/2009 | Mager et al. |
| 2009/0118387 | A1* | 5/2009 | Sakakibara ......... C08G 18/283 521/170 |
| 2011/0160633 | A1 | 6/2011 | Schonberger et al. |
| 2011/0171277 | A1 | 7/2011 | Schonberger |
| 2011/0178451 | A1 | 7/2011 | Robinson et al. |
| 2011/0184080 | A1* | 7/2011 | Schonberger ....... C08G 18/755 521/90 |
| 2011/0201715 | A1 | 8/2011 | Schoenberger et al. |
| 2012/0226251 | A1 | 9/2012 | Rivest et al. |
| 2013/0131206 | A1 | 5/2013 | Niesten et al. |
| 2014/0246151 | A1 | 9/2014 | Passmann et al. |

FOREIGN PATENT DOCUMENTS

| | | |
|---|---|---|
| CN | 102159165 | 8/2011 |
| CN | 102197074 | 9/2011 |
| EP | 1964580 A1 | 12/2010 |
| GB | 2376632 A | 10/2004 |
| GB | 2382989 A | 3/2005 |
| JP | H04503763 A | 7/1992 |
| JP | 2000045503 A | 2/2000 |
| JP | 2006517427 | 7/2006 |
| JP | 2009510087 | 3/2009 |
| JP | 2012529921 A | 11/2012 |
| JP | 2013078366 A | 5/2013 |
| JP | 2013517097 A | 5/2013 |
| JP | 2013532216 A | 8/2013 |
| JP | 3187099 U | 10/2013 |
| JP | 2015080580 A | 4/2015 |
| JP | 2015521079 A | 7/2015 |
| JP | 2015181790 A | 10/2015 |
| JP | 2015186511 A | 10/2015 |
| WO | 1990010424 A1 | 9/1990 |
| WO | 2004047695 A1 | 6/2004 |
| WO | 2004/060225 A1 | 7/2004 |
| WO | 2004060412 A1 | 7/2004 |
| WO | 2007/033679 A2 | 3/2007 |
| WO | 2007033678 A2 | 3/2007 |
| WO | 2009007018 A1 | 6/2009 |
| WO | 2010003559 A1 | 1/2010 |
| WO | 2010147535 A1 | 12/2010 |
| WO | 2011090991 A2 | 7/2011 |
| WO | 2012027114 A1 | 3/2012 |
| WO | 2013/180937 A1 | 12/2013 |
| WO | 2013180832 A1 | 12/2013 |
| WO | 2014075684 A1 | 5/2014 |

OTHER PUBLICATIONS

En Iso 9073-3 "Textiles—Test methods for nonwovens—Part 3: Determination of tensile strength and elongation", (1989).

* cited by examiner

A

B

ABSORBENT ALIPHATIC POLYURETHANE FOAM PRODUCT

CROSS-REFERENCE TO RELATED APPLICATIONS

This application is a 35 U.S.C. § 371 National Phase Entry of the International Application No.PCT/GB2017/051694 filed Jun. 9, 2017, which designates the U.S., and which claims benefit under 35 U.S.C. § 119 of the Great Britain Application No. 1610184.2 filed Jun. 10, 2016, the contents of each of which are incorporated herein by reference in their entirety.

FIELD OF THE INVENTION

The present invention relates to a product. In particular, the present invention relates to absorbent articles and products, in particular profiled foam-based absorbent products having certain production advantages.

BACKGROUND

Foams are widely employed in the manufacture of absorbent articles such as wound dressings and sanitary products.

A hurdle in the manufacture of such absorbent articles is the provision of a suitable trade-off between the degree of absorbency and the comfort perceived by the wearer. Traditionally-shaped foam pads and dressings suffer from the problems of pressure points at the area of contact with the wearer's skin and/or lack of air circulation to the dressed or covered region.

WO 2007/033678 relates to a wound dressing which expands controllably during wetting. The dressing comprises a backing layer and an absorbent layer, wherein the absorbent layer comprises a series of discrete foam pads covering at least 50% of the wound-facing surface.

WO 2007/033679 relates to a bevelled-edged foam wound dressing, in which the density of the foam at the edges is higher than the density in the central part of the foam. The high density at the edges prevents leakage of wound exudate.

WO 2004/047695 discloses a dressing for joints or curved portions of the body comprising a multiplicity of indentations which define a series of adhesive islands. The indentations and adhesive islands are on a surface facing away from the skin.

A rate-limiting step in the production of such absorbent articles is the need to contour, shape or emboss the foam after the article has been released from the production line.

WO 2010/003559 describes a process for producing polyurethane foams based on low molecular weight aliphatic diisocyanates, in which the foams undergo a curing process. The foams are formed into sheets after they have been prepared. US 2002/0160037 describes a polyurethane matrix wound dressing which is formed into a mould prior to curing. WO2007/033678 also describes the contouring of foam pads prior to curing.

Accordingly, there is a need in the art for a profiled absorbent foam product which is both comfortable and allows sufficient air flow to the dressed or covered area, and which can be produced by a time-efficient, cost-effective manufacturing process.

SUMMARY OF INVENTION

The present inventors have found that profiled absorbent foams and foam products, in particular aliphatic foams and foam products, exhibit an advantageous capillary motor effect during the absorption of fluid.

Furthermore, the present inventors have found that absorbent foams and foam products, in particular aliphatic foams and foam products, can be shaped, profiled, embossed or contoured in-line with the product manufacturing process.

Accordingly, in a first aspect, the present invention provides an absorbent aliphatic polyurethane foam product having at least one profiled surface. The foam product of the invention may be obtainable or obtained by a process of the invention.

In a second aspect, the present invention provides a process for producing a profiled absorbent polyurethane foam product, said process comprising the steps of:
  a) providing a foamed polyurethane prepolymer composition;
  b) curing the foamed composition;
  c) profiling the foamed composition;
  d) drying the foamed composition
wherein said profiling step (c) occurs before said drying step (d).

In a third aspect, the present invention provides an apparatus for producing a profiled absorbent polyurethane foam product, said apparatus comprising:
  a) curing means;
  b) drying means;
  c) profiling means;
wherein said profiling means (c) are operably located between the curing means and the drying means.

DETAILED DESCRIPTION

Figure 1A:
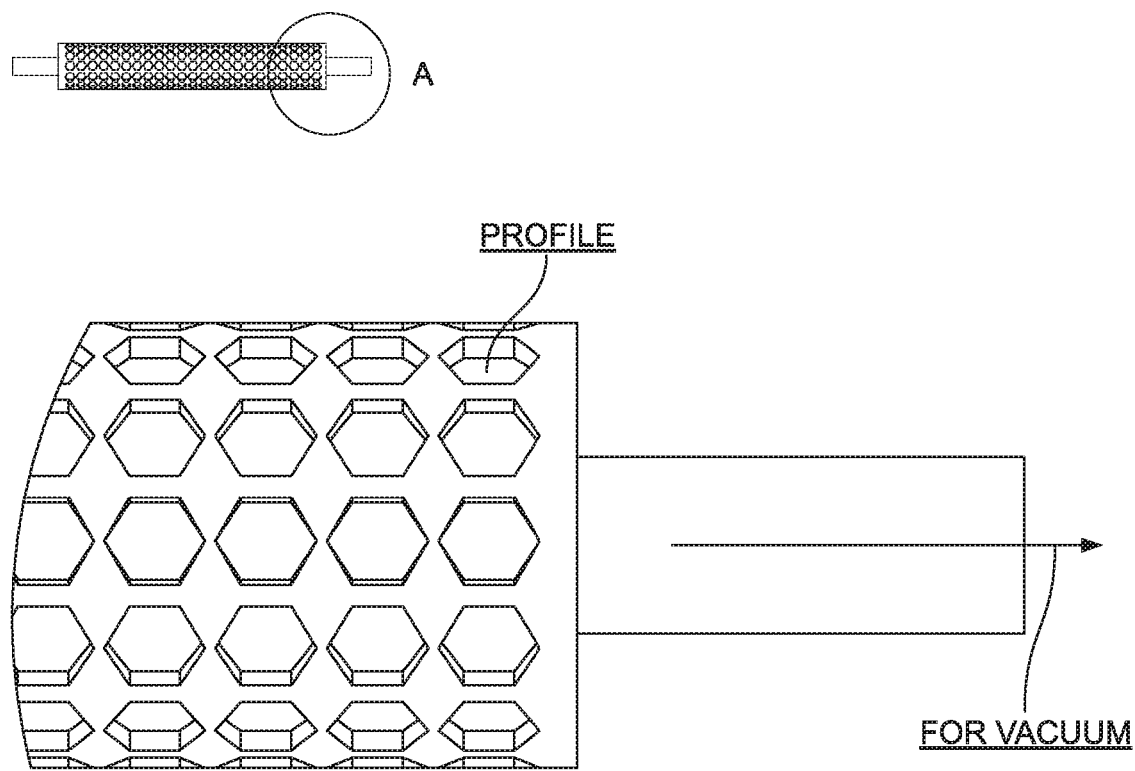
FIG. 1 is an annotated diagram of a profiled roller to be used in a foam line production assembly. A Close-up design of honeycomb profile roller. B Positioning of profiled roller on the production line.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The profiled absorbent polyurethane foam product of the present invention may be a rudimentary foam pad comprising no additional layers or active ingredients.

In some embodiments, the absorbent product of the invention may comprise additional layers such as release paper layers, backing layers, film, supportive film, alginate-based layers, adhesive layers or additional absorbent layers.

The profiled surface of the absorbent product may be in any textured, embossed, relief pattern or design.

The absorbent product may comprise one or more additives or active ingredients.

Profiled Surface

By "profiled" it is meant that the absorbent foam or foam product of the invention is, for example, shaped, contoured, textured, imprinted, raised, indented, embossed or formed in relief. Such profiling may be effected by contacting the foam with a plate or roller. Such a plate or roller may comprise on its surface a template relief pattern to be embossed or imprinted on the foam. In some embodiments, the term "profiled" does not encompass the moulding or casting of the foam prior to curing, a method which is equally applicable to the process of the present invention.

The profiled surface of the present invention may comprise one or more raised portions or relief portions, also known herein as non-compressed portions. Such raised or relief portions may be know in the art as bumps or dimples, creating a so-called "hill-and-valley" effect on the product surface.

The profiled surface may be defined, for example, in terms of the structure and shape of such "hills" and "valleys".

The raised (non-compressed) portions may be raised with respect to the valleys or indentations, also known herein as the compressed portions. The raised portions may be on the skin- or wound-facing surface of the absorbent product. Whilst the raised portion(s) or "hills" may come into contact with the wearer's skin, the indentations or "valleys" may not come into contact with the wearer's skin and thus provide improved air flow to the wound, skin, region exuding fluid or region covered by the product.

Accordingly, in one embodiment, the profiled surface comprises one or more raised (non-compressed) portions and/or one or more indented (compressed) portions. The profiled surface may comprise one or more indented (compressed) portions and one or more raised (non-compressed) portions.

The absorbent foam product of the present invention has an advantageous or favourable capillary motor action or effect during the absorption of fluid. Without wishing to be bound by theory, it is now believed that fluid which contacts a compressed portion or region of condensed foam (i.e. a "valley") is drawn away from the compressed portion into the non-compressed portions or regions (i.e. "hills") by this capillary motor effect. Where a non-compressed portion has absorbed the maximum capacity of fluid (i.e. the hill is "full" of fluid), excess fluid that cannot be further absorbed by the "full" hill is drawn by the capillary motor effect to a different hill that has not yet absorbed fluid to its maximum capacity. The non-compressed portions of the profiled surface of the foam product thereby act as reservoirs for absorbed fluid. In this way, absorbed fluid is more evenly distributed around the foam product than it would in a non-profiled product.

Accordingly, in certain embodiments, when an indented or compressed region of an absorbent product of the invention contacts a wound or a region exuding fluid, exudate is drawn away from the wound or a region exuding fluid into adjacent raised or non-compressed areas not in contact with wound or a region exuding fluid. This feature of the profiled absorbent product thereby provides an advantage of increased comfort for the wearer, in contrast to other forms of dressing, as unpleasant exudate is drawn away from contact with the affected area.

The profiled surface of the absorbent foam product of the present invention may be in any textured, embossed, relief pattern or shaped design. However, certain shapes and designs are described below as being associated with particular technical advantages.

In the same or different embodiment, the profiled surface of the invention comprises a pattern of connected or interconnected indentations (compressed portions) formed into said surface to provide one or more, such as a plurality of, raised portions (non-compressed portions or islands). The raised (non-compressed) portions of the invention may be discrete raised portions.

The pattern of connected or interconnected indentations may comprise a first indentation formed into said surface in a first direction; a second indentation formed into said surface in a second direction that is different from the first direction; and a third indentation formed into said surface in a third direction that is different from the first direction and the second direction.

The first, second and third indentations may meet or intersect. The first, second and third indentations may be in the form of a pattern of connected indentations being non-linear, for example non-linear across their entire length. The first, second and third indentations may progress in at least three main directions. The pattern of connected indentations may have an angled propagation.

Each of the raised (non-compressed) portions may be of any shaped cross-section, particularly of shapes which are able to tessellate with one another, more particularly of uniformly-shaped cross-section. For example, the raised portions may be of essentially circular, polygonal, hexagonal, octagonal, rectangular, square or triangular cross-section. Those of circular or hexagonal cross-section are preferred.

Even more preferably, the indentations are in the form of a honeycomb pattern, preferably in which the indentations define a pattern of raised (non-compressed) portions having the maximum thickness of the absorbent product.

The pattern of connected indentations may cover over half, such as substantially all, of the wound- or skin-facing surface of the absorbent product of the invention.

The plurality of raised portions may be separated from one another by said indentations, wherein said plurality of raised portions (dimples) are arranged in one of a vertical, horizontal or diagonal sequence.

Figure 4:
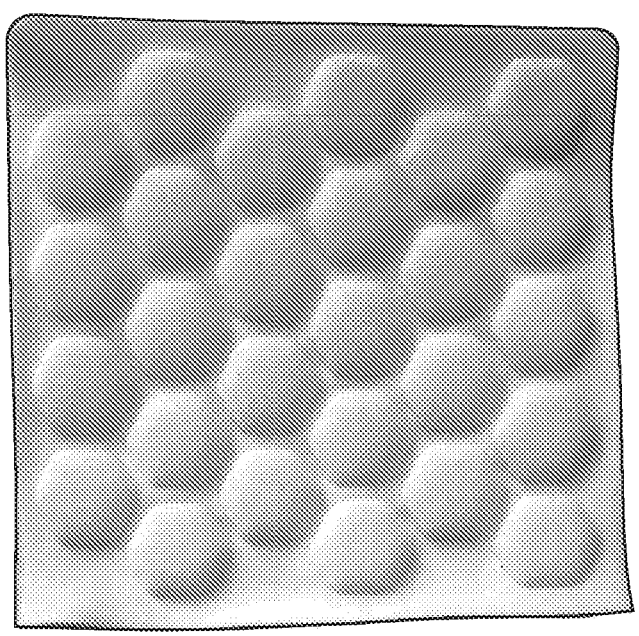
FIG. 4 depicts a foam dressing having a "dimpled" profile or profile having raised portions and indentations. A Clean dressing. B Dressing challenged with synthetic blood.
Figure 4:
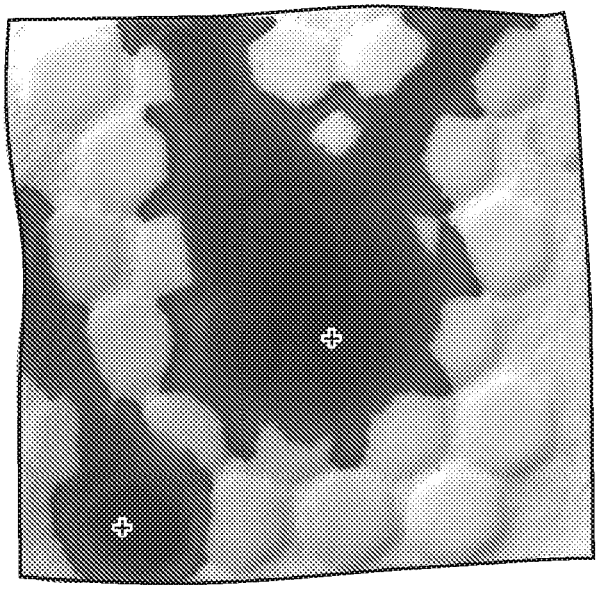

A dimpled absorbent foam product (dressing) in accordance with the present invention is depicted in FIG. 4.

Properties

By "absorbent" it is meant that the foam or foam product is capable of taking up fluid into its cell structure. Suitably, the foam product will retain said fluid, for example the foam product may absorb and retain up to 30 times its own weight in fluid. In some embodiments, the foam product of the invention absorbs more than or equal to 15 times it own weight, preferably more than or equal to 20 times its own weight, of fluid.

Suitable absorption tests for measuring the absorbency of a product of the invention are known in the art. The test may comprise weighing the product and/or calculating its surface area, placing the product into a saline solution, for example an (excess) solution of 0.9 wt. % saline at about 36° C., placing the product into an incubator, for example at about 35° C. for about 30 minutes, suspending the product vertically, then re-weighing the product, to calculate the absorbency e.g. in g/g or g/100 cm$^2$.

Following this absorption test, the product may then be uniformly compressed with a 4 kg mass e.g. for about 30 seconds and reweighed. Optionally the product may be subjectively compressed by hand and re-weighed. This enables calculation of the fluid retention (%) of the product.

The thickness increase (%) of the product on absorption may be determined by measuring the thickness (e.g. in mm) of the product before and after the absorption test described above.

Accordingly, the foam product of the present invention may have an absorbency of more than about 85, preferably about 85 to about 135, preferably about 95 to about 125, preferably about 105 to about 115, most preferably about 110 g fluid per 100 cm$^2$ surface area of foam product (g/100 cm$^2$).

Additionally or alternatively, the foam product of the present invention may have an absorbency of more than 14.5, preferably about 14.5 to about 16.5, preferably about 15 to about 16, preferably about 15.5 g fluid per g foam product (g/g).

Additionally or alternatively, the absorbent foam product of the present invention may have a fluid retention of more than about 58, preferably about 58 to about 70, preferably about 60 to about 67, preferably about 63%.

Additionally or alternatively, the absorbent foam product of the present invention may have a thickness increase after an absorption test of more than about 11, preferably about 11 to about 30, preferably about 15 to about 25, preferably about 19%.

In a further test, the speed of absorption of a fluid droplet expelled from a syringe (without a needle loaded therein) may be measured. The fluid droplet may be a saline droplet. The syringe may have a gauge or aperture of about 2 mm. The test comprises dropping the droplet onto the product and timing the interval from contact of the droplet with the product surface to complete absorption of the droplet into the product.

Accordingly, the absorbent foam product of the present invention may have a speed of fluid droplet absorption of less than about 4.3, preferably less than about 4, preferably less than about 3, preferably less than about 2 seconds, even more preferably less than about 1 second.

The absorbent foam product of the present invention has an advantageous or favourable capillary motor action or effect during the absorption of fluid.

In an embodiment, the present invention provides an absorbent aliphatic polyurethane foam product having one or more of the following properties:
  (i) density of about 100 to 180 kg/m$^3$;
  (ii) absorbency of greater than about 85 g/100 cm$^2$ (e.g. as measured by the absorption test described herein);
  (iii) absorbency of greater than about 14.5 gig (e.g. as measured by the absorption test described herein);
  (iv) fluid retention of greater than about 58% (e.g. as measured by the fluid retention test described herein);
  (v) thickness increase after absorption test of greater than about 11% (e.g. as measured by the thickness increase test described herein);
  (vi) speed of absorption of fluid droplet of less than about 4.3 seconds (e.g. as measured by the fluid droplet absorption test described herein);
preferably wherein the foam product is profiled.

The raised or non-compressed portions of the profiled foam product may have a density of about 100 to about 140 kg/m$^3$. The indented or compressed portions of the foam product may have a density of about 140 to about 180 kg/m$^3$.

The raised or non-compressed portions of the profiled foam product may have an absorbency (e.g. as determined by the absorbency test described herein) of more than about 40, 50, 60, 70 or 80, such as more than about 85, such as about 80 to about 135, such as about 80 to about 100 such as about 85 to about 95 g fluid per 100 cm$^2$ surface area of foam product (g/100 cm$^2$). The indented or compressed portions of the foam product may have an absorbency of less than about 40, such as less than about 20, such as about 10 to about 20, such as about 15 g/100 cm$^2$.

The raised or non-compressed portions of the profiled foam product may have an absorbency (e.g. as determined by the absorbency test described herein) of more than 5, 6, 7, 8, 9, 10, 11 or 12, such as more than 14, such as more than 14.5, such as about 14 to about 16, such as about 14 to about 15, such as about 14.5 g fluid per g foam product (g/g). The indented or compressed portions of the foam product may have an absorbency of less than about 5, such as less than about 4, such as about 2 to about 4, such as about 3 g/g.

The raised or non-compressed portions of the profiled foam product may have a thickness increase after absorption test (e.g. as determined by the thickness increase test described herein) of more than about 10, such as more than about 40, such as about 60 to about 100, such as about 70 to about 90, such as about 80%. The indented or compressed portions of the foam product may have a thickness increase after absorption test of less than about 60, such as less than about 40, such as about 30 to about 40%.

The raised or non-compressed portions of the profiled foam product may have a speed of absorption of a fluid droplet (e.g. as determined by the fluid droplet absorption test described herein) of less than about 4.3, such as less than about 4, such as less than about 3 seconds and/or more than about 0.8, such as more than about 1, such as more than about 2 seconds. The indented or compressed portions of the foam product may have a speed of absorption of less than about 2, such as less than about 1.5, such as less than about 1, such as about 0.5 to about 1 second, such as about 0.75 seconds.

The raised or non-compressed portions of the profiled foam product may have a fluid retention (e.g. as determined by the fluid retention test described herein) of more than about 15, such as more than about 20, 30, 40 or 50, such as more than about 58, such as about 58 to about 70, such as about 60 to about 70, such as about 65%. The indented or compressed portions of the foam product may have a fluid retention of less than about 50, such as less than about 20, such as about 5 to about 15, such as about 10 to about 15%.

The tests or assays described above may also be carried out according to the tests described in EN ISO 527-2.

Accordingly, the present invention provides an absorbent aliphatic polyurethane foam product having at least one profiled surface, wherein the profiled surface comprises one or more raised or non-compressed portions and one or more indented or compressed portions, wherein:

(i) the indented or compressed portions have a higher density than the raised or non-compressed portions; and/or (ii) the indented or compressed portions have a lower absorbency than the raised or non-compressed portions; and/or (iii) the indented or compressed portions have a reduced thickness increase after absorption test when compared to the raised or non-compressed portions; and/or (iv) the indented or compressed portions have a faster speed of absorption of a fluid droplet when compared to the raised or non-compressed portions; and/or (v) the indented or compressed portions have a lower fluid retention than the raised or non-compressed portions.

The present invention also provides an absorbent aliphatic polyurethane foam product having at least one profiled surface, wherein the profiled surface comprises one or more raised or non-compressed portions and/or one or more indented or compressed portions, wherein the raised or non-compressed portions have one or more of the following properties:

(i) density of about 100 to about 140 kg/m$^3$;

(ii) absorbency of greater than about 40 g/100 cm' (e.g. as measured by the absorption test described herein);

(iii) absorbency of greater than about 5 g/g (e.g. as measured by the absorption test described herein);

(iv) fluid retention of greater than about 50% (e.g. as measured by the fluid retention test described herein);

(v) thickness increase after absorption test of greater than about 40% (e.g. as measured by the thickness increase test described herein);

(vi) speed of absorption of fluid droplet of about 1 to about 4.3 seconds (e.g. as measured by the fluid droplet absorption test described herein)

and/or wherein the indented or compressed portions have one or more of the following properties:

(i) density of about 140 to about 180 kg/m$^3$;

(ii) absorbency of less than about 40 g/100 cm' (e.g. as measured by the absorption test described herein);

(iii) absorbency of less than about 5 g/g (e.g. as measured by the absorption test described herein);

(iv) fluid retention of less than about 50% (e.g. as measured by the fluid retention test described herein);

(v) thickness increase after absorption test of less than about 40% (e.g. as measured by the thickness increase test described herein);

(vi) speed of absorption of fluid droplet of less than about 1 second (e.g. as measured by the fluid droplet absorption test described herein).

The foam or foam product, such as the profiled aliphatic polyurethane foam layer of the present invention may have a maximum thickness of 10, 9, 8, 7, 6, 5, 4, 3 or 2 mm or less. For example, the maximum thickness of the raised or non-compressed portion may be 10, 9, 8, 7, 6, 5, 4, 3 or 2 mm or less. The maximum thickness of the indented or compressed portion may be 5, 4, 3, 2, 1.5, 1 or 0.5 mm or less. In a preferred embodiment, the maximum thickness of the raised or non-compressed portion is between about 3 to about 6 mm, such as about 4.4 or 4.5 mm and the maximum thickness of the indented or compressed portion is between about 1 to about 2 mm, such as about 1.3 or 1.5 mm.

Herringbone or V-Shaped Profiling

In some embodiments of the invention, the profiled surface comprises a pattern of connected or interconnected raised (non-compressed) portions formed into said surface.

In an embodiment, the profiled surface may comprise a central elongate indented (compressed) portion extending substantially from one edge of the absorbent product to the (diametrically) opposite or substantially parallel edge, and a plurality of additional elongate indented (compressed) portions extending from the central indented (compressed) portion, preferably substantially to one or more edges of the product. The additional elongate indented (compressed) portions may be parallel to one another. Each of the additional indented (compressed) portions may form an acute angle with the central indented (compressed) portion at the point of its extension from the central indented (compressed) portion.

Figure 13:
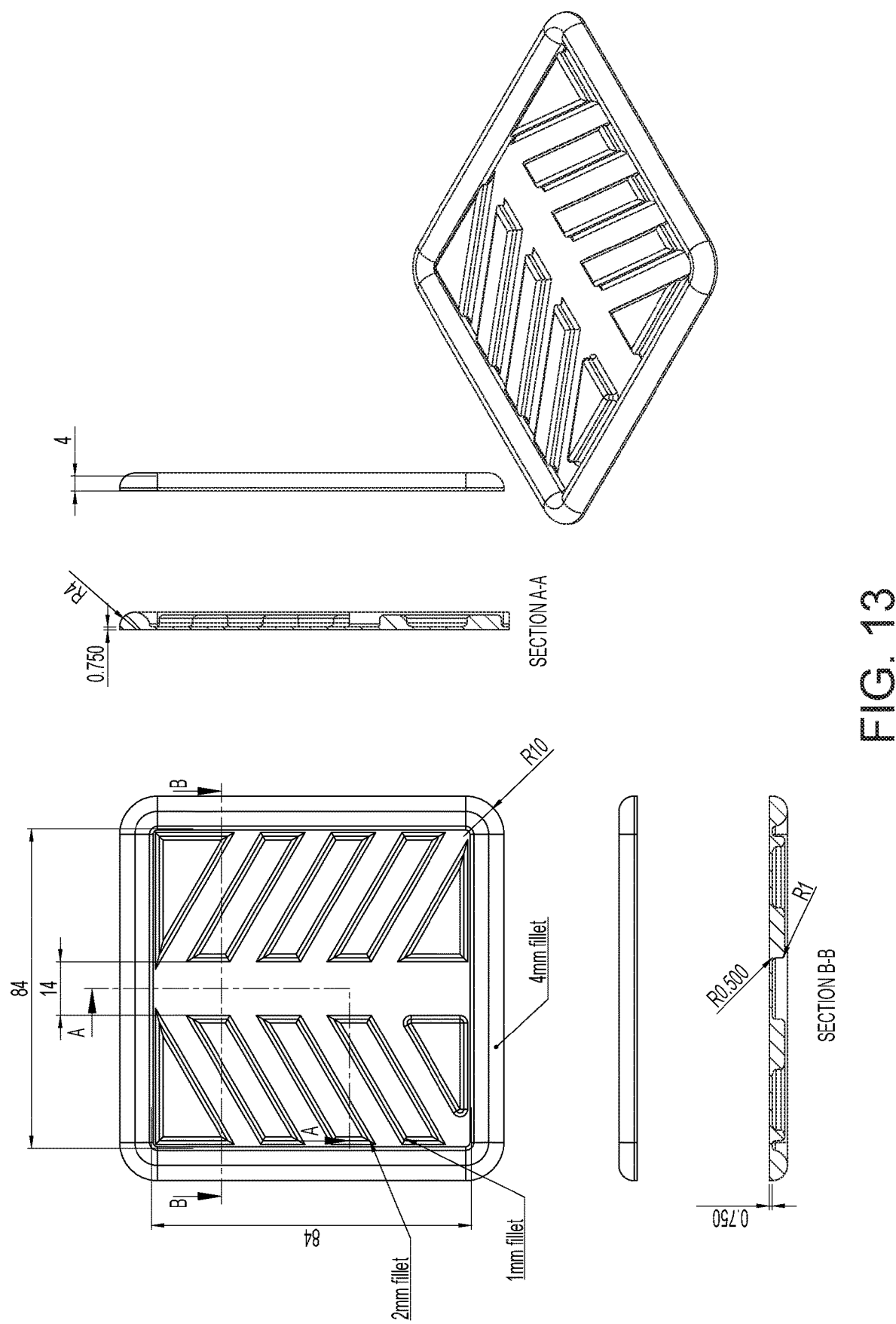
FIG. 13 depicts a foam dressing having a herringbone or "V-shaped" profile. Measurements are in mm.

Accordingly, the profiled surface may comprise V-shaped or herringbone profiling. The resulting appearance is that of a fish backbone and ribs, as depicted in FIG. 13.

In another embodiment, the profiled surface may comprise a central elongate raised (non-compressed) portion extending substantially from one edge of the absorbent product to the (diametrically) opposite or substantially parallel edge, and a plurality of additional elongate raised (non-compressed) portions extending from the central raised (non-compressed) portion, preferably substantially to one or more edges of the product. The additional elongate raised (non-compressed) portions may be parallel to one another. Each of the additional raised (non-compressed) portions may form an acute angle with the central raised (non-compressed) portion at the point of its extension from the central raised. (non-compressed) portion.

Figure 5:
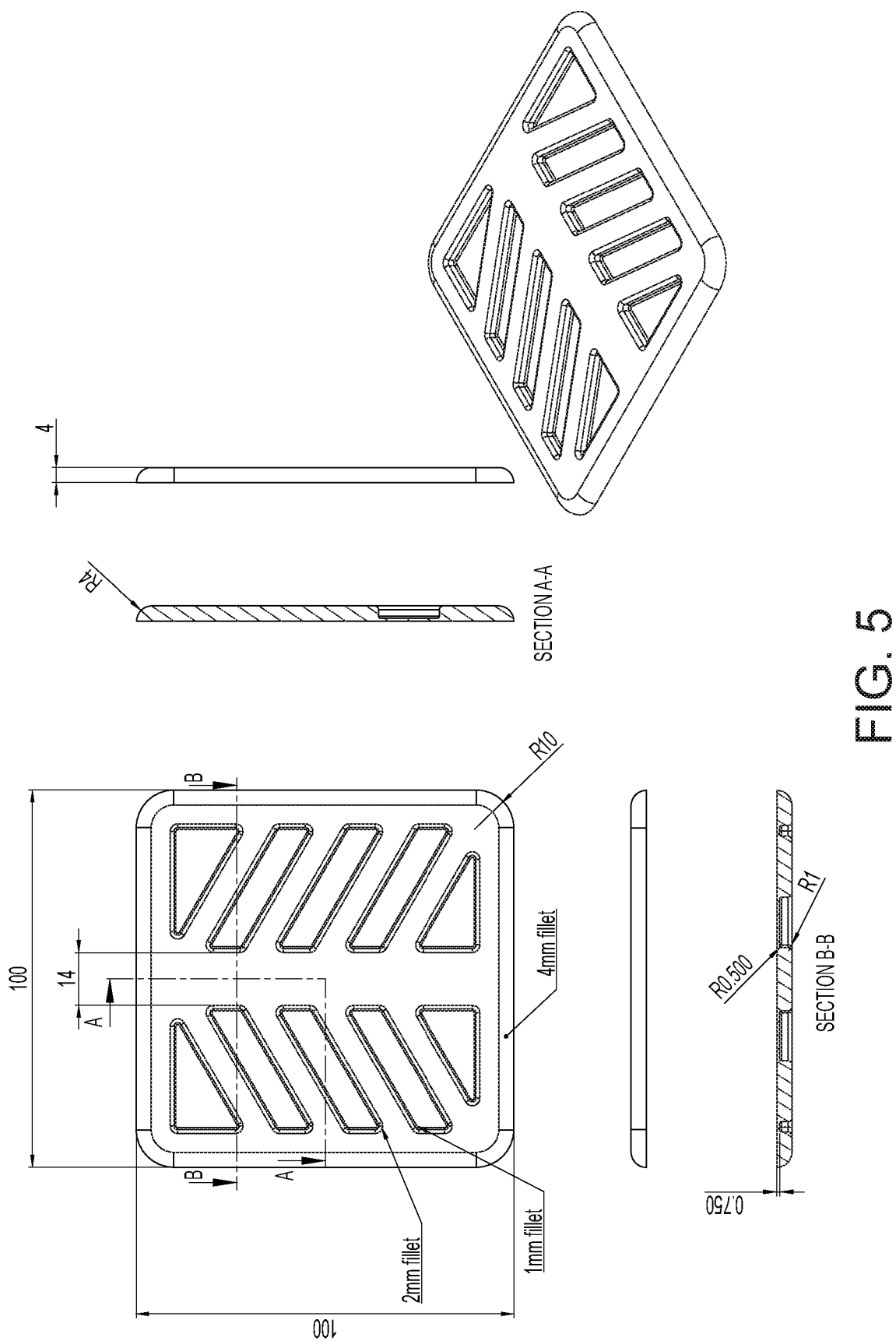
FIG. 5 depicts a foam dressing having an inverse herringbone or "V-shaped" profile. Measurements are in mm.

Accordingly, the profiled surface may comprise V-shaped or herringbone profiling. The resulting appearance of this so-called "inverse" V-shaped or herringbone profiling is that of a fish backbone and ribs, as depicted in FIG. 5.

The herringbone or V-shaped design advantageously provides an in situ drainage system for fluid and/or exudate. The additional elongate raised or indented portions (the ribs) provide a series of channels sufficiently large for the exudate fluid to be pulled away from the wound or wet site under negative pressure without clogging up with potential solid components of the exudate. The indented (compressed) portions provide 'drains' into the raised (non-compressed) portion(s), where a substantial amount of fluid or exudate can be retained.

Flower Shaped Profiling

The profiled surface may comprise a plurality of indented (compressed) regions radiating from an indented (compressed) region positioned essentially centrally on said surface.

The radiating indented (compressed) regions may or may not extend to an edge of the absorbent product. Preferably, they do not.

There may be 2 or more, such as 3, 4, 5, 6, 7, 8, 9, 10, 11 or 12 or more elongate indented regions. In a preferred embodiment, there are 8 elongate indented regions.

The central indented region may be of any diameter, such as about 5 to about 50 mm in diameter, such as about 15 to about 40 mm in diameter, such as about 25 to about 35 mm in diameter, such as about 30 to about 25 mm in diameter, such as about 32.6 mm in diameter.

The radiating indented regions may be elongate. The central indented region may be essentially circular or essentially polygonal. The number of sides of the polygon will depend on the number of elongate indented regions. For example, when there are 8 elongate indented regions, the central indented region may be octagonal. The combination of the elongate indented regions radiating from the central circular indented region gives the impression of spokes or petals radiating from a central *nexus* or node.

Figure 12:
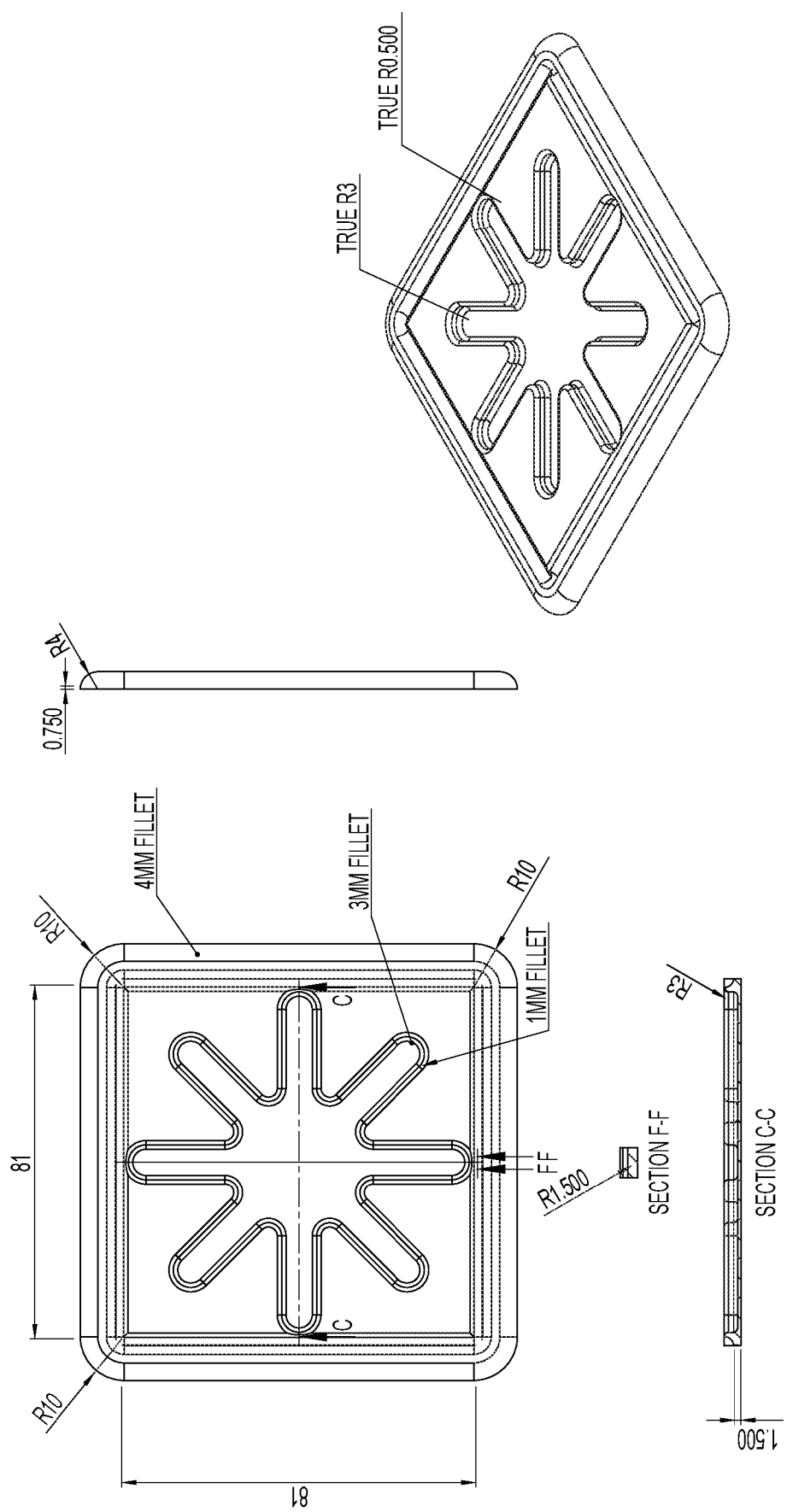
FIG. 12 depicts a foam dressing having a "flower-shaped" profile. Measurements are in mm.

Accordingly, the profiled surface may have "flower" shaped profiling. The resulting appearance is exemplified in FIG. 12 and FIG. 20.

Figure 6:
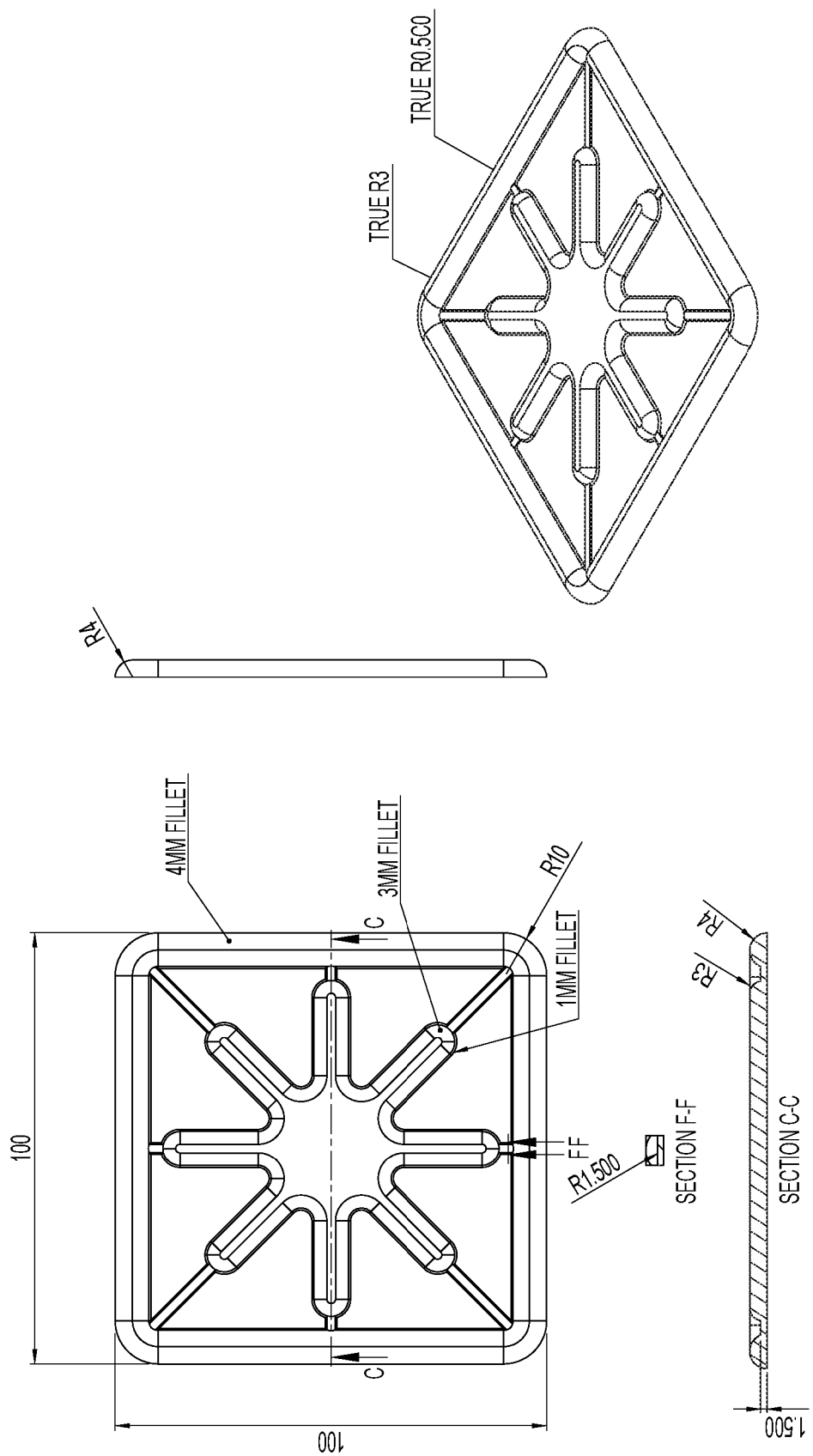
FIG. 6 depicts a foam dressing having an inverse "flower-shaped" profile. Measurements are in mm.

Also contemplated herein is so-called "inverse" flower shaped profiling, i.e. wherein the profiled surface comprises a plurality of non-compressed or raised regions radiating from a raised region positioned essentially centrally on said surface. The radiating raised regions may or may not extend to an edge of the absorbent product. Preferably, they do not. The resulting appearance is exemplified in FIG. 6.

In all embodiments, the absorbent product, including any raised portions or indentations may be non-adhesive.

Bevelled Edge

The profiled surface of the invention may comprise a bevelled edge. Straight edges on a wound dressing may lead to undesirable indentation marks on the patient's skin and subsequent discomfort. Accordingly, a bevelled-edged dressing provides improved comfort.

Traditional foam products are of relatively high density. Advantageously, the density of the foam of the present invention may be as low as 80 kg/m$^3$, 100 kg/m$^3$, 120 kg/m$^3$ or 140 kg/m$^3$, leading to reduced pressure on the area of the absorbent product in contact with the skin.

Accordingly the present invention also provides an absorbent aliphatic polyurethane foam product having at least one profiled surface, wherein said profiled surface comprises a bevelled edge, further wherein the density of the foam is between about 80 and about 400 kg/m$^3$, preferably 80 to about 140 kg/m$^3$, such as about 120 to about 140 kg/m$^3$, such as about 80 to about 99 kg/m$^3$. Such density values may refer to the density of the foam or foam product as a whole, or may refer to the density of the central portion of the foam or foam product (i.e. not at the edge portion).

In some embodiments, the density of the foam at the edge portion, for example the bevelled edge, is around 5 times the density of the foam at the central portion. For example the density at the edge portion may be at least about 400 kg/m$^3$, such as at least about 500 kg/m$^3$.

The edge portion of an absorbent product of the present invention may be defined as the outmost 1 cm of the rim, such as the outmost 0.8 cm, the outmost 0.7 cm, the outmost 0.6 cm, the outmost 0.5 cm, the outmost 0.4 cm, the outmost 0.3 cm, or even the outmost 0.2 cm.

In some embodiments, the bevelled edge of the present invention is comprised in or within the outmost 0.2 cm of the rim of the absorbent product.

Thus, preferably, in the absorbent product of the present invention, the profiled surface comprises a bevelled edge, preferably wherein the bevel is comprised within the outermost 0.2 cm of the rim of the product, preferably wherein the density of the foam is between about 80 to about 500 kg/m$^3$.

Figure 3:
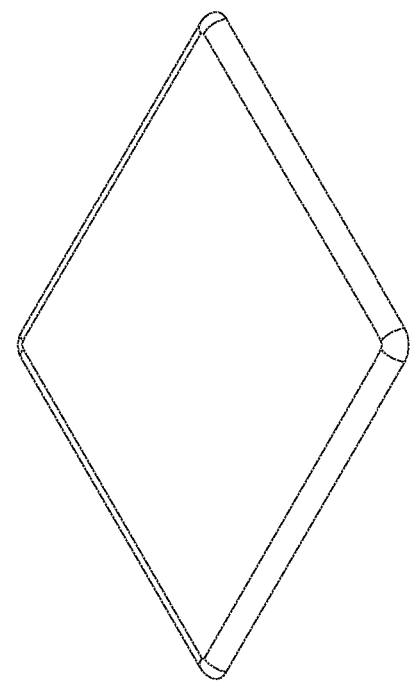
FIG. 3 depicts a foam dressing having a bevelled edge. Measurements are in mm.
Figure 3:
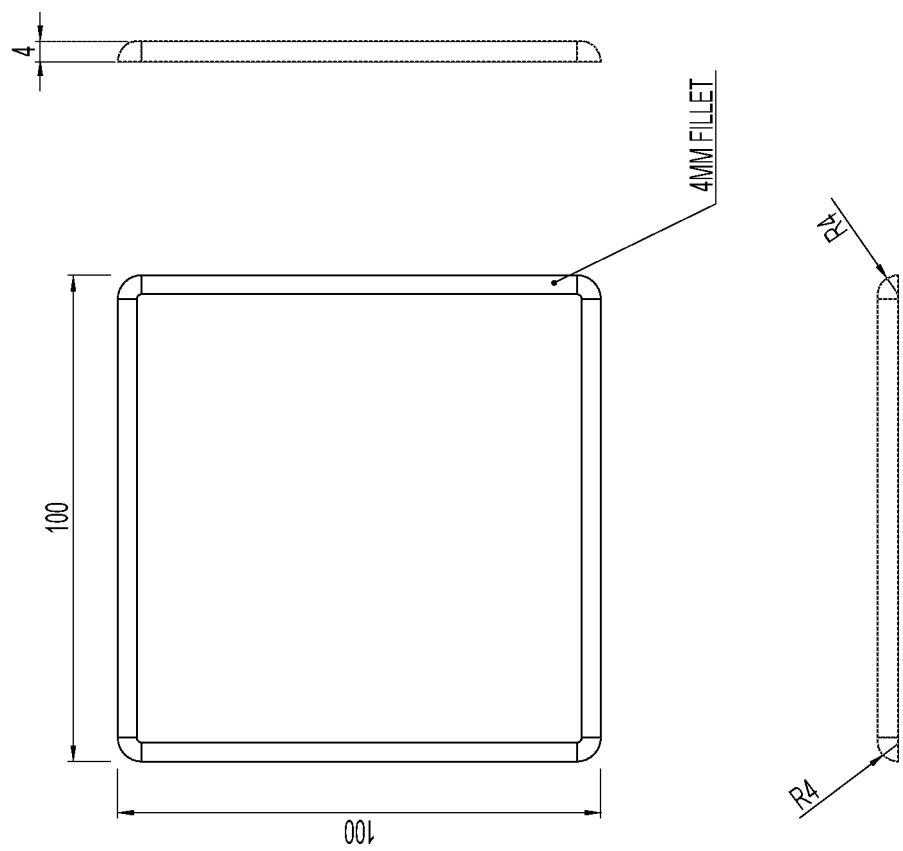

A bevelled edged absorbent product (dressing) in accordance with the present invention is depicted in FIG. 3.

The bevel may be on the non skin or wound-facing surface of the product or dressing or alternatively on the skin or wound-facing surface of the product or dressing.

Additional technical design embodiments of the present invention may negate the need for a high-density bevel.

The above design embodiments (e.g. bevelled edge, dimples, herringbone, flower) may be used in combination with one another. In particular, the bevelled edge design may be used in combination with one or more of the dimple, herringbone or flower designs.

Additives and Active Ingredients

The product of the present invention may comprise or be impregnated with one or more additives and/or active ingredients, for example a pharmaceutical medicament.

This feature provides for a combined medical treatment of e.g. a wound, where the dressing absorbs (wound) exudate and the pharmaceutical medicaments will be applied to the wound, skin or region exuding fluid.

The additives and/or active ingredients, such as pharmaceutical medicaments, can e.g. be incorporated in the foam (e.g. before or during curing) or may be provided as a separate layer or coating on the absorbent product.

Accordingly, the process of the present invention may comprise incorporating one or more additives and/or active ingredients into the foam product. The additives/active ingredients may be provided in or incorporated into the prepolymer composition. Incorporation of the additives/active ingredients may take place before- or during curing. The process of the present invention may comprise coating the foam product with one or more additives/active ingredients. The additives/active ingredients may be pharmaceutical medicaments.

Examples of such pharmaceutical medicaments include a cytokine such as a growth hormone or a polypeptide growth factor such as TGF, FGF, PDGF, EGF, IGF-1, IGF-2, colony stimulating factor, transforming growth factor, nerve stimulating growth factor and the like. Other medicaments such as bacteriostatic or bactericidal compounds, e.g. iodine, iodopovidone complexes, chloramine, chlorhexidine, silver salts such as sodium silver zirconium phosphate (available as Alphasan), sulphadiazine, silver nitrate, silver acetate, silver lactate, silver sulphate, silver sodium thiosulphate or silver chloride, zinc or salts thereof, metronidazole, sulpha drugs, and penicillins, tissue-healing enhancing agents, e.g. RGD tripeptides and the like, proteins, amino acids such as taurine, vitamins such ascorbic acid, enzymes for cleansing of wounds or affect areas, e.g. pepsin, trypsin and the like, proteinase inhibitors or metalloproteinase inhibitors such as Illostat or ethylene diamine tetraacetic acid, pain relieving agents such as NSAIDs (e.g. Ibuprofen), lidocaine or chinchocaine, emollients, retinoids or agents having a cooling effect.

The additive/active ingredient may also comprise odour controlling or odour reducing material e.g. a deodorant or perfume.

Particularly preferred additives/active ingredients include antiseptics such as chlorhexidine, biocidal actives such as silver or salts thereof, carbon (charcoal), superabsorber and agents which provide electrical conductivity such as salt (sodium chloride).

The superabsorber (also known as a superabsorbent polymer or hydrogel) is preferably a polyacrylic acid sodium salt.

The one or more additives/active ingredients of the invention may be water degradable. In this regard, an aliphatic foam product of the present invention provides an advantage over aromatic foam products in that less water is used in formation of aliphatic foams and aliphatic foams have a shorter drying time. In aliphatic foams, water degradable additives/active ingredients are less exposed to water and thus more readily maintain their maximum efficiency in aliphatic foams than in aromatic foams.

Additional Layers

The foam product of the invention may comprise additional layers of material layered or bonded onto the profiled absorbent aliphatic polyurethane foam.

In some embodiments, these additional layers comprise films or alginate-based layers. In further embodiments, these additional layers are adhesive. In a preferred embodiment, the foams and foam products of the invention are laminated with at least one film layer.

The films or alginate-based layers may be on the top or bottom of the profiled absorbent aliphatic polyurethane foam. Preferably, the profiled absorbent aliphatic polyurethane foam is between one film layer and one alginate-based layer.

Suitable films include those from Covestro under the name AQUACEL®. Suitable alginate-based layers include those from Speciality Fibres and Materials Ltd (SFM).

Accordingly, the present invention provides an absorbent product comprising a polyurethane layer, a film layer and an alginate-based layer. Preferably the polyurethane layer is layered between the film layer and the alginate layer. Preferably the polyurethane is aliphatic polyurethane such as hydrophilic aliphatic polyurethane. Preferably the product does not comprise any adhesive, either between the layers or on the external surfaces of the product.

Additional Polyurethane Layer

In some embodiments, the additional layer consists of or comprises a polyurethane foam. The additional layer of polyurethane foam may be a different polyurethane foam to that of the profiled absorbent aliphatic polyurethane foam layer. Preferably, the additional (or second) polyurethane layer has different properties to the profiled absorbent aliphatic polyurethane foam layer, allowing the properties of the different polyurethanes to be advantageously combined in the foam product of the invention.

The additional or second polyurethane layer may be an aliphatic polyurethane layer. The additional or second polyurethane layer may be thermoformable or thermoplastic. By "thermoformable" it is meant that the foam has the ability to be shaped using heat. The additional polyurethane layer may have a microporous cell structure. Such a feature enables fast fluid transport.

In some embodiments, the additional (or second) polyurethane layer has different absorbency and/or fluid retention and/or thickness increase after absorption test and/or speed of absorption of a fluid droplet when compared to the profiled polyurethane layer.

For example, the additional polyurethane layer may have lower absorbency than the profiled layer, in particular the non-compressed portion(s) of the profiled layer. The additional polyurethane layer may have lower fluid retention than the profiled layer, in particular the non-compressed portion(s) of the profiled layer. The additional polyurethane layer may have reduced thickness increase after absorption test when compared to the profiled layer, in particular the compressed and/or non-compressed portion(s) of the profiled layer. The additional polyurethane layer may have the same or lower speed of absorption of a fluid droplet when compared to the profiled layer, in particular the non-compressed portion(s) of the profiled layer.

The additional polyurethane layer may have a density of 80 to 200 kg/m$^3$, such as 100 to 140 kg/m$^3$, such as about 120 kg/m$^3$.

In addition or in the alternative, the additional polyurethane layer may have an absorbency of less than about 85 g/100 cm$^2$, such as less than about 50 g/100 cm$^2$, such as 10 to 40 g/100 cm$^2$, such as 20 to 30 g/100 cm$^2$, such as about 26 g/100 cm$^2$.

In addition or in the alternative, the additional polyurethane layer may have an absorbency of less than about 14.5 g/g, such as less than about 10 g/g, such as 5 to 10 g/g, such as about 9.3

In addition or in the alternative, the additional polyurethane layer may have a fluid retention of less than about 58%, such as 50 to 55%, such as about 53%.

In addition or in the alternative, the additional polyurethane layer may have a thickness increase after absorption test of less than about 11%, such as less than about 10, 9, 8, 7, 6, 5, 4 or 3%, or more preferably less than about 2%.

In addition or in the alternative, the additional polyurethane layer may have a speed of absorption of a fluid droplet (for example a saline droplet) of less than about 2 seconds, such as less than 1.5 or 1 second.

In addition or in the alternative, the additional polyurethane layer may have a tensile strength of about 0.5 to about 1 MPa, such as about 0.7 MPa. Suitable tests for determining tensile strength are known in the art, such as that described in test EN ISO 527-2.

In addition or in the alternative, the additional polyurethane layer may have an elongation at break of about 200 to about 400%, such as about 250 to about 350%, such as about 300%. Suitable tests for determining elongation at break are known in the art, such as that described in test EN ISO 9073-3.

Accordingly, in a preferred embodiment, the additional polyurethane layer of the invention has one or more of the following properties:

(i) density of about 80 to about 200 kg/m$^3$;

(ii) absorbency of less than about 85 g/100 cm$^2$;

(iii) absorbency of less than about 14.5 g/g;

(iv) fluid retention of less than about 58%;

(v) thickness increase after absorption test of less than about 11%;

(vi) speed of absorption of a fluid droplet (for example a saline droplet) of less than about 2 seconds;

(vii) tensile strength of about 0.5 to about 1 MPa;

(viii) elongation at break of about 200 to about 400%.

Properties of a particular additional polyurethane layer of the invention are shown in Table 1 below.

TABLE 1

Properties of FD103 foam.

| | Absorbancy (g/100 cm$^2$) | Absorbancy (g/g) | Fluid Retention after 4 Kg and Subjective compression (%) | Thickness incresase (%) | Speed of absorbtion (seconds) | Tensile strength (MPa) DIN EN ISO527-2 | Elongation at break (%) |
|---|---|---|---|---|---|---|---|
| SENTIENT FD103 Eumar Technology | 26 | 9.3 | 53 | <2 | <2 | 0.7 | 300 |

The additional, polyurethane layer may be manufactured from a prepolymer composition comprising 5-chloro-2-methyl-3(2H)-isothiazolone and 2-methyl-3(2H)-isothiazolone, preferably in a 3:1 ratio.

The additional polyurethane layer may be manufactured by mechanical frothing of a prepolymer composition in aqueous solution. The frothed composition may then be dried at about 120° C. for 10-30 minutes (depending on foam thickness). The permeability of the foam may therefore be controlled by the mixing/frothing step, in that the size of the air bubbles may be adjusted according to mixing time. Niax L-6889 compolymer may be used as a stabilizer during the production process.

Suitable additional or second polyurethane layers include polyurethane foams manufactured from BAYMEDIX® FD103 prepolymer.

In an embodiment, the profiled polyurethane layer is manufactured from BAYMEDIX® FP505 prepolymer and the additional layer is manufactured from BAYMEDIX® FD103 prepolymer.

Non-Woven Material

In some embodiments, a non-woven material may be provided as an additional layer. The non-woven material prevents expansion of the profiled polyurethane foam, upon absorption of fluid, in the plane of the non-woven material layer. Therefore, upon absorption of fluid, the profiled polyurethane foam bonded to a layer of non-woven material will expand in the axis perpendicular to the plane of the non-woven material (i.e. in the vertical plane or Z-axis), but not in the plane of the non-woven material (i.e. in the horizontal plane or X-Y axis). Where a foam product of the invention contacts the body, this expansion lifts the product from contact with the body, facilitating air flow to the body and potentially alleviating pressure on sensitive areas, and thereby providing another advantage of the present invention.

The non-woven material may comprise polyester, such as a dry polyester textile. The non-woven material may comprise hydrophilic fibres. The non-woven material may have a density of 30 to 50 g/m$^3$, such as a density of about 40 g/m$^3$. The non-woven material may have a thickness of 0.5 to 2 mm, such as 1 to 1.5 mm, such as about 1.2 mm. The non-woven material may have a tensile strength of 40 to 50 N/5 cm, such as about 42 N/5 cm in the machine direction (MD) and of 4.5 to 5.5 N/5 cm, such as about 4.9 N/5 cm in the cross direction (CD). The non-woven material may have an elongation at break (Fmax) of 15 to 25%, such as about 19% in the MD and of 60 to 70%, such as about 65% in the CD. Suitable non-woven materials include those from Dry-Web or twe hygiene, such as DRY WEB T28F.

It follows from the description of the above additional layers that the profiled surface of the foam or foam product is not necessarily the surface which is exposed to the air, the skin, the wound or region of fluid exudation. For example, the profiled surface may have one or more of the additional layers described above laminated or formed directly thereon, thus shielding the profiled surface from view.

Accordingly, in one embodiment, the profiled surface may face, or come into direct contact with the wound, skin, affected area or region exuding fluid. In another embodiment, whilst the profiled surface faces the wound, skin, affected area or region exuding fluid, it does not come into direct contact with it, due to the additional layer(s). A region exuding fluid may be e.g. a boil, ulcer, breast or vagina.

Shaping

The absorbent product of the present invention may be an essentially flat product or dressing (not taking into account any of the raised portions or indentations described above), designed to be applied to a flat or slightly curved area of the body, for example for use as an incontinence product. In some embodiments, the absorbent product is shaped or contoured or is able to adapt to the contour of the skin on a protruding part of the body e.g. a breast, nipple, or around a joint, e.g. a heel, knuckle, elbow, knee or part of the hand. In some embodiments, the absorbent product comprises a thermoformable layer that is shaped to the contour of the skin on a protruding part of the body. The thermoformable layer may be the outer layer of the product whilst a profiled absorbent polyurethane foam forms the inner layer that contacts the skin. The outer layer thereby provides shape to the product whilst the inner layer provides cushioning and absorbs exudate.

Accordingly, the present invention also provides heel pads capable of adapting to the contour of a heel, and lactation pads capable of adapting to the contour of a breast or nipple. In an embodiment, the product comprises a first layer of absorbent aliphatic polyurethane foam having at least one profiled surface laminated to or juxtaposed with a second polyurethane layer, preferably wherein the second layer is thermoformable. A suitable first layer is BAYMEDIX® FP505 and a suitable second layer is BAYMEDIX® FD103. Such pads may also comprise one or more of the design embodiments described above (e.g. e.g. bevelled edge, dimples, herringbone, flower). Particularly preferred is a heel pad having dimples or raised portions.

Particular Products

In a preferred embodiment, the profiled absorbent product of the present invention is a dressing (such as a dressing for a wound, boil or ulcer), a pad (such as a breast pad, lactation pad, sanitary pad, incontinence pad, bed sore prevention pad or heel pad), a nappy (diaper), or other sanitary or hygiene product (e.g. a feminine hygiene product such as a maternity towel).

Particularly preferred embodiments are described in more detail below.

Dressing for a Boil or Ulcer

In one embodiment, the profiled absorbent product of the invention is a dressing for a boil or ulcer, wherein the profiled surface faces the boil or ulcer. The profiled surface may have any of the profiling shapes or designs described herein. Preferably, the profiled surface of the dressing has the "flower shaped" profiling described herein.

Preferably, the profiled foam is an aliphatic foam described herein, such as those manufactured from BAYMEDIX® FP505 prepolymer. The dressing may comprise a single layer of such aliphatic polyurethane foam. The dressing may be provided with one or more of the additional layers described herein. Preferably, the profiled foam layer is the innermost layer of the dressing (i.e. nearest the skin). One or more of the layers may be provided with one or more of the additives/active ingredients described herein.

In such embodiments, the boil or ulcer sits in the central indented (compressed) region of the "flower". Exudate from the boil or ulcer contacting the central indented region is drawn away from the point of contact into the surrounding raised portions of the dressing by capillary motor action. Exudate is thereby removed from contact with the boil or ulcer, providing increased comfort for the wearer over non-profiled dressings.

Breast Pad

In one embodiment, the profiled absorbent product of the invention is a breast pad, wherein the profiled surface faces the breast. The profiled surface may have any of the profiling shapes or designs described herein. Preferably, the profiled surface of the breast pad has the "flower shaped" profiling described herein.

In one embodiment, the breast pad comprises a single layer of aliphatic polyurethane foam. An example of the single layer of aliphatic polyurethane foam is that manufactured from BAYMEDIX® FP505 prepolymer.

In another embodiment, the breast pad comprises two layers of aliphatic polyurethane foam, wherein the first layer comprises the profiled surface that faces the breast as described above. Preferably the second layer is thermoformable. Preferably the second layer is shaped so as to conform to the contours of a breast. A suitable first layer is manufactured from BAYMEDIX® FP505 prepolymer and a suitable second layer is manufactured from BAYMEDIX® FD103 prepolymer.

The breast pad may be provided with one or more of the additional layers described herein. Preferably, the profiled foam layer is the innermost layer of the dressing (i.e. nearest the skin, breast or nipple). One or more of the layers may be provided with one or more of the additives/active ingredients described herein. Accordingly, the breast pad—such as the first layer of the breast pad—may comprise an odour controlling or odour reducing material e.g. a deodorant or perfume.

In the above embodiments, the nipple of the breast may sit in the central indented (compressed) region of the "flower". Exudate from the nipple contacting the central indented region is drawn away from the point of contact into the surrounding raised portions of the breast pad by capillary motor action. Exudate is thereby removed from contact with the nipple, providing increased comfort for the wearer over non-profiled breast pads. The breast pad of the invention may be provided as an insert or inner for a bra.

Sanitary Pad or Towel

In one embodiment, the profiled absorbent product of the invention is a sanitary pad or sanitary towel. The profiled surface may have any of the profiling shapes or designs described herein. Preferably, the profiled surface of the sanitary pad or towel has the "V-shaped" or herringbone profiling described herein.

In an embodiment, the sanitary pad or towel comprises a first polyurethane layer laminated to or juxtaposed with a second polyurethane layer, wherein the first layer comprises the profiled surface, the second layer is laminated onto the profiled surface of the first layer, and the second layer forms the vaginal contact surface.

Preferably, the second layer has different absorbency, such as higher or lower absorbency and/or lower fluid retention than the first layer. A suitable first layer is an aliphatic polyurethane foam described herein, such as that manufactured from BAYMEDIX® FP505 prepolymer. A suitable second layer is a thermoformable foam, such as that manufactured from BAYMEDIX® FD103 prepolymer.

The sanitary pad may be provided with one or more of the additional layers described herein. Preferably at least the vaginal contact surface is layered with a non-woven material that reduces the viscosity of the menstrual fluid. One or more of the layers may be provided with one or more of the additives/active ingredients described herein.

Equally, the sanitary pad or towel may be provided with a non-woven material as both the inner layer (i.e. the vaginal contact surface) and the outer layer. In another embodiment, the inner layer is a non-woven material and the outer layer is a polythene layer. Suitable non-woven materials are described herein.

Bed Sore Prevention Pad

In one embodiment, the profiled absorbent product of the invention is a bed sore prevention pad, wherein the profiled surface faces the body.

The profiled surface may have any of the profiling shapes or designs described herein. Preferably, the profiled surface of the bed sore prevention pad comprises an essentially central indented (compressed) region surrounded by dimpled profiling as described herein, for example wherein the raised portions are of essentially circular or hexagonal cross-section. The central indented (compressed) region may have a larger surface area than any one of the dimples. The dimples themselves may not be uniform surface area. For example, there may be two populations of dimples, one having a larger surface area than the other.

The central indented region accommodates a protruding part of the body that might otherwise form a pressure point between the body and the bed. The surrounding dimpled profiling spreads the pressure from the body weight across multiple points, thereby preventing any single point of contact between the body and the bed forming a pressure point that might develop a bed sore.

The central indented (compressed) region may be elongate, such as essentially rectangular or elliptical in cross-section, for example to accommodate the (lumbar) spinal region or coccyx of the wearer. The dimples nearest to the central indented region may be the ones with the largest surface area. In one embodiment, all or part of the central indented region is provided or replaced with an aperture or opening. In another embodiment, all or part of the central indented region is provided with a foam cushion. The foam cushion, opening or aperture may be elongate, such as essentially rectangular or elliptical in cross-section. The embodiment having the foam cushion may be more suitable for patients already having an existing bed sore wound. The bed sore prevention pad may be provided with a perforated cutting line, which may extend through the central indented region.

Figure 14:
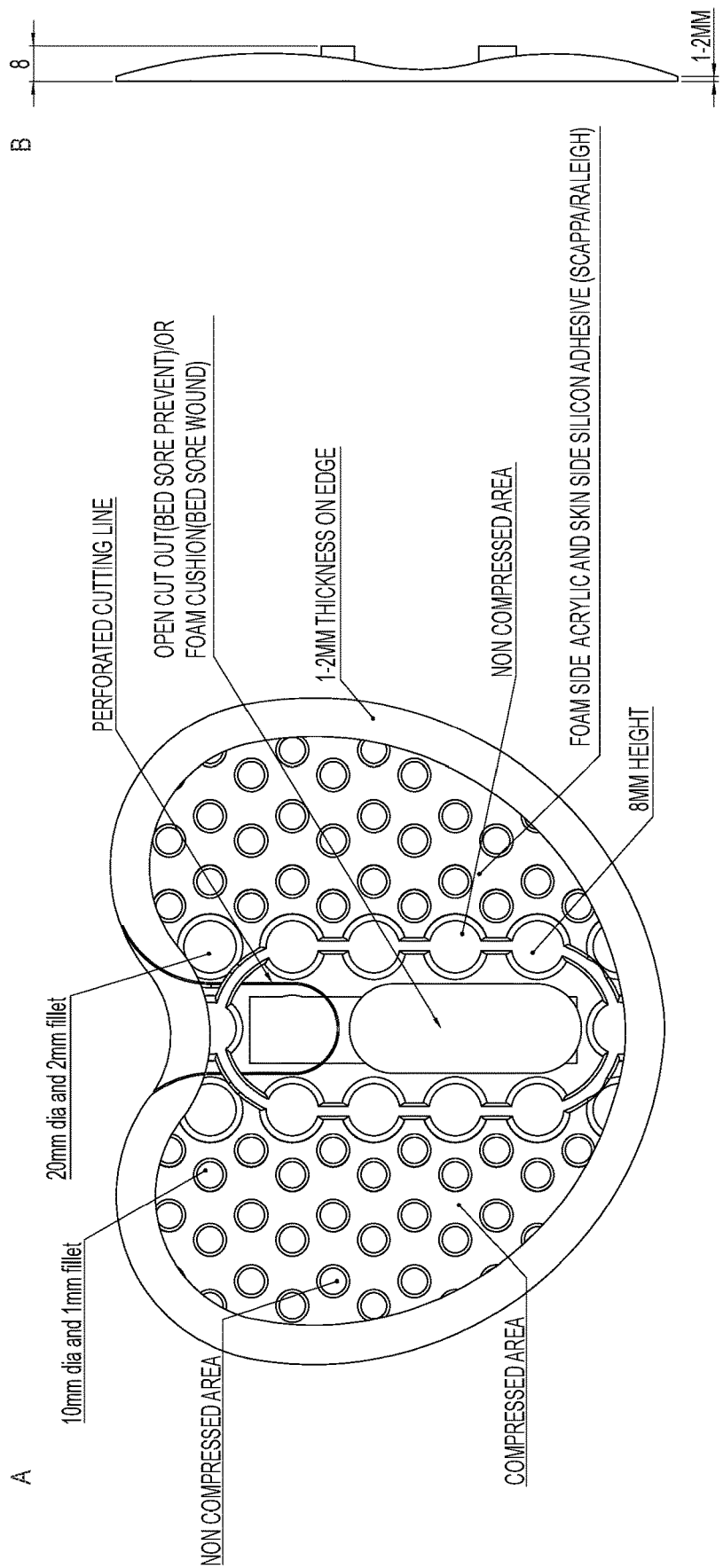
FIG. 14A depicts a bed sore prevention pad/bed sore wound pad of the invention.
FIG. 14B depicts a cross-section through the pad. Measurements are in mm.

An example of a bed sore prevention pad of the present invention is provided in FIG. 14.

The bed sore prevention pad may be provided with one or more of the additional layers described herein. One or more of the layers may be provided with one or more of the additives/active ingredients described herein.

Heel Pad

In one embodiment, the profiled absorbent product of the invention is a heel pad, wherein the profiled surface faces the heel. The profiled surface may have any of the profiling shapes or designs described herein. Preferably, the profiled surface of the heel pad has the dimpled profiling described herein.

In an embodiment, the heel pad comprises a first polyurethane layer laminated to or juxtaposed with a second polyurethane layer, wherein the first layer comprises the profiled surface that faces the heel. Preferably the second layer is thermoformable. Preferably the second layer is shaped so as to conform to the contours of a heel. A suitable first layer is that manufactured from BAYMEDIX® FP505 prepolymer and a suitable second layer is that manufactured from BAYMEDIX® FD103 prepolymer.

The bed sore prevention pad may be provided with one or more of the additional layers described herein. One or more of the layers may be provided with one or more of the additives/active ingredients described herein.

Process for Producing Profiled Foam

Preploymer Composition

In one embodiment, the polyurethane foam of the present invention is aliphatic polyurethane foam, preferably hydrophilic aliphatic polyurethane foam. As such, the polyurethane foam of the present invention may be prepared by a method comprising reacting an aliphatic isocyanate-based prepolymer with water and surfactant in the presence of a catalyst.

Aliphatic foams are particularly advantageous in the operation of present invention because they do not suffer any volume shrinkage after expansion. They also provide rapid and high absorption of physiological saline or wound fluid without the need for superabsorbent polymers. Aliphatic foams also exhibit superior tensile strength and a distinct lack of the classic yellowing observed upon exposure to UV waves. Aliphatic foams can also be cured and dried in an advantageously short time frame, since they typically comprise low amounts of water prior to drying (e.g. about 10 wt. %).

Processes for producing aliphatic foams are known in the art, for example from WO 2010/003559 and WO 2009/007018, which are each incorporated herein by reference.

The foam of the present invention may be a composition comprising:

A) isocyanate-functional prepolymers having a weight fraction of low molecular weight aliphatic diisocyanates having a molar mass of 140 to 278 g/mol of below 1.0% by weight based on the prepolymer, preferably obtainable by reaction of:
A1) low molecular weight aliphatic diisocyanates having a molar mass of 140 to 278 g/mol with
A2) di- to hexafunctional, preferably tri- to hexafunctional polyalkylene oxides having an OH number of 22.5 to 112, preferably of 31.5 to 56, and an ethylene oxide content of 50 to 100 mol %, preferably of 60 to 85 mol %, based on the total amount of oxyalkylene groups present;

B) water;
C) optionally catalyst;
D) optionally surfactant;
E) optionally heterocyclic 4-ring or 6-ring oligomers of low molecular weight aliphatic diisocyanates having a molar mass of 140 to 278 g/mol;
F) optionally $C_8$-$C_{22}$ monocarboxylic acids or their ammonium or alkali metal salts or $C_{12}$-$C_{44}$ dicarboxylic acids or their ammonium or alkali metal salts;
G) optionally mono- or polyhydric alcohols.

The prepolymer may be an isocyanate-based prepolymer, such as an aliphatic isocyanate prepolymer, such as an aliphatic diisocyanate prepolymer, such as a low molecular weight aliphatic diisocyanate prepolymer. A particularly preferred (low molecular weight) aliphatic diisocyanate is hexamethylene diisocyanate (HDI).

The water used as component B) can be used as such, as water of crystallization of a salt, as solution in a dipolar aprotic solvent or else as an emulsion. Preferably, the water is used as such or in a dipolar aprotic solvent. It is very particularly preferred to use water as such.

To speed urethane formation, component C) may utilize catalysts. The catalysts in question are typically compounds with which a person skilled in the art is familiar from polyurethane technology. Preference here is given to sodium hydrogen carbonate and/or citric acid. Preferably, component C) comprises both sodium hydrogen carbonate (e.g. at a concentration of about 1.5 wt. % of the total prepolymer composition) and citric acid (e.g. at a concentration of about 3.5 wt. % of the total prepolymer composition).

Compounds of component D) can be used to improve foam formation, foam stability or the properties of the resulting polyurethane foam, in which case such additives can in principle be any known anionic, cationic, amphoteric and nonionic surfactants and also mixtures thereof. Preference is given to using Pluronic® PE 6800. The surfactant may be used at a concentration of about 40 wt. % of the total prepolymer composition.

The present invention also provides a process for producing a profiled absorbent polyurethane foam product described herein, further comprising the steps of:
providing a composition comprising at least one polyurethane prepolymer;
optionally foaming the composition or allowing the composition to foam.

The composition comprising at least one polyurethane prepolymer may preferably comprise or consist of components A), B), C) and D). In such an embodiment, the composition may be provided by mixing at components A), B), C) and D) in any order. The components B), C) and D) are preferably mixed with each other prior to addition to A).

The components are typically used in a ratio of 9 parts of A) to 1 part of a mixture of B), C) and D). Preferably, the components are used in a ratio of 7 parts of A) to 1 part of a mixture of B), C) and D), even more preferably 5 parts of A) to 1 part of a mixture of B), C) and D). Such ratios may have the advantage of improving the tensile strength and/or providing a favourable density of the resulting foam.

In some embodiments, component A) is BAYMEDIX®, in particular BAYMEDIX® FP505. In the same or different embodiment, components B), C) and D) are provided as a single composition, for example from AQUACEL®.

Foaming

Foaming can in principle be effected by means of the carbon dioxide formed in the course of the reaction of the isocyanate groups with water, but the use of further blowing agents is likewise possible. It is thus also possible in principle to use blowing agents from the class of the hydrocarbons such as $C_3$-$C_6$ alkanes, for example butanes, n-pentane, isopentane, cyclopentane, hexanes or the like, or halogenated hydrocarbons such as dichloromethane, dichloromono-fluoromethane, chlorodifluoroethanes, 1,1-dichloro-2,2,2-trifluoroethane, 2,2-di chl oro-2-fl uoro-eth an e, particularly chlorine-free hydrofluorocarbons such as difluoromethane, trifluoromethane, difluoroethane, 1,1,1,2-tetrafluoroethane, tetrafluoroethane (R 134 or R 134a), 1,1,1,3,3-penta-fluoropropane (R 245 fa), 1,1,1,3,3,3-hexafluoropropane (R 256), 1,1,1,3,3-pentafluorobutane (R 365 mfc), heptafluoropropane, or else sulphur hexafluoride. Mixtures of these blowing agents can also be used.

Preferably, foaming is an inevitable result of the mixing of the aforementioned components of the prepolymer composition. In such embodiments the process of the present invention does not require the use of blowing agents. However, in other embodiments, a blowing agent may be used, for example to achieve suitably low density foam.

The density of the foam of the present invention may be such that the absorption capacity is optimised, and air flow between the foam product and the skin, capillary action of the exudate, and wearer comfort are maximised. Thus, the absorbent foam product of the present invention may have a density of between about 80 and about 500 kg/m$^3$, such as between about 80 and about 400 kg/m$^3$ such as between about 100 and about 200 kg/m$^3$, or between about 100 and about 150 kg/m$^3$. In a preferred embodiment of the invention, the density is between about 80 and about 100 kg/m$^3$ or between about 80 and about 99 kg/m$^3$.

In a bevelled edged absorbent product of the invention, the density of the foam may be higher at the edge than in the centre of the product. As such, the density values above may relate to the density of the foam in the centre of the product (i.e. in the central portion).

Foaming may take place during the curing process.

Curing

In the context of the present invention, the term "curing" refers to the stage in the foam production process in which the polyurethane prepolymer composition is allowed to cream, gel and rise to its final size. Accordingly, the curing stage ends when the foam has risen to its final size. For example, curing may be considered to have ended prior, such as immediately prior, to the profiling step; or prior, such as immediately prior to the (active) drying step (e.g. when the foam enters a hot air tunnel or oven).

The polyurethane prepolymer composition may be poured into a casting or moulding immediately prior to the curing step. The curing step may be carried out on a curing means, for example a curing track or curing conveyor.

Curing may be measured by three distinct parameters:
i) Cream time;
ii) gel time;
iii) rise time.

Cream time is the time when the isocyanate mixture begins to change from the liquid state to a creamy state and starts to expand subsequently. Gel time is the time the foam starts to stiffen and CO2 production may be at its highest rate. Rise time is the time the foam takes to reach to its maximum height.

In some embodiments, the whole of the curing process may take between about 30 seconds and about 5 minutes, for example between about 1 and about 3 minutes, preferably about 2 minutes.

Preferably, the maximum height of the foam of the present invention at the end of curing is between about 2 to about 4 mm, for example about 3 mm.

Curing may take place at a temperature of between about 15° C. to about 45° C. In preferred embodiments, curing takes place a room temperature (e.g. about 15° C. to about 22° C.), or at between about 40° C. to about 45° C.

Drying

The term "drying" in the context of the present invention is meant to refer to the stage of active drying of the foam, i.e. the subjecting of the foam to a specific drying step or drying means intended to remove water or moisture from the foam. This is most commonly effected using heat.

Drying may be effected using a drying means, such as a heat tunnel, hot air tunnel, drying oven or source of infrared radiation.

In some embodiments, the whole of the drying process may take between about 30 seconds and about 2 minutes, for example between about 45 seconds and about 1 minute 30 seconds, preferably about 1 minute.

Drying may take place at a temperature of between about 80° C. to about 120° C. In preferred embodiments, drying takes place between about 90° C. to about 110° C., preferably at about 100° C. In the context of the present invention, no substantial or quantifiable drying is considered to occur during the curing process.

In one embodiment, there may be stepwise changes (e.g. increases) in drying temperature during the drying stage, for example there may be a period of drying at 80° C., followed by a period at 100° C., followed by a period at 120° C.

Profiling

One advantage is that the foam of the present invention can be profiled before the foam has been dried.

Profiling may be achieved by any suitable profiling means, for example a roller or plate. The roller or plate may be made of any suitable material. Such a plate or roller may comprise on its surface a template relief pattern to be embossed or imprinted on the foam, when in use said plate or roller comes into contact with the foam.

Preferably, the profiling step of the process of the present invention is carried out using a roller, such as a profiling roller or emboss roller. In other embodiments, the roller may be described by the shape which it embosses or imparts onto the foam. For example, a honeycomb roller comprises on its surface a plurality of recesses of hexagonal cross-section, so as in use to emboss a plurality of raised hexagonal portions onto the foam. In a related embodiment, the roller is not a kiss-cutting roll.

In one embodiment, the roller is heated, for example for a period of 0.5 seconds-1 second, for example to any temperature above room temperature. The heating may be effected by means of a heating cartridge, such as a cartridge inserted into the roller.

Figure 1B:
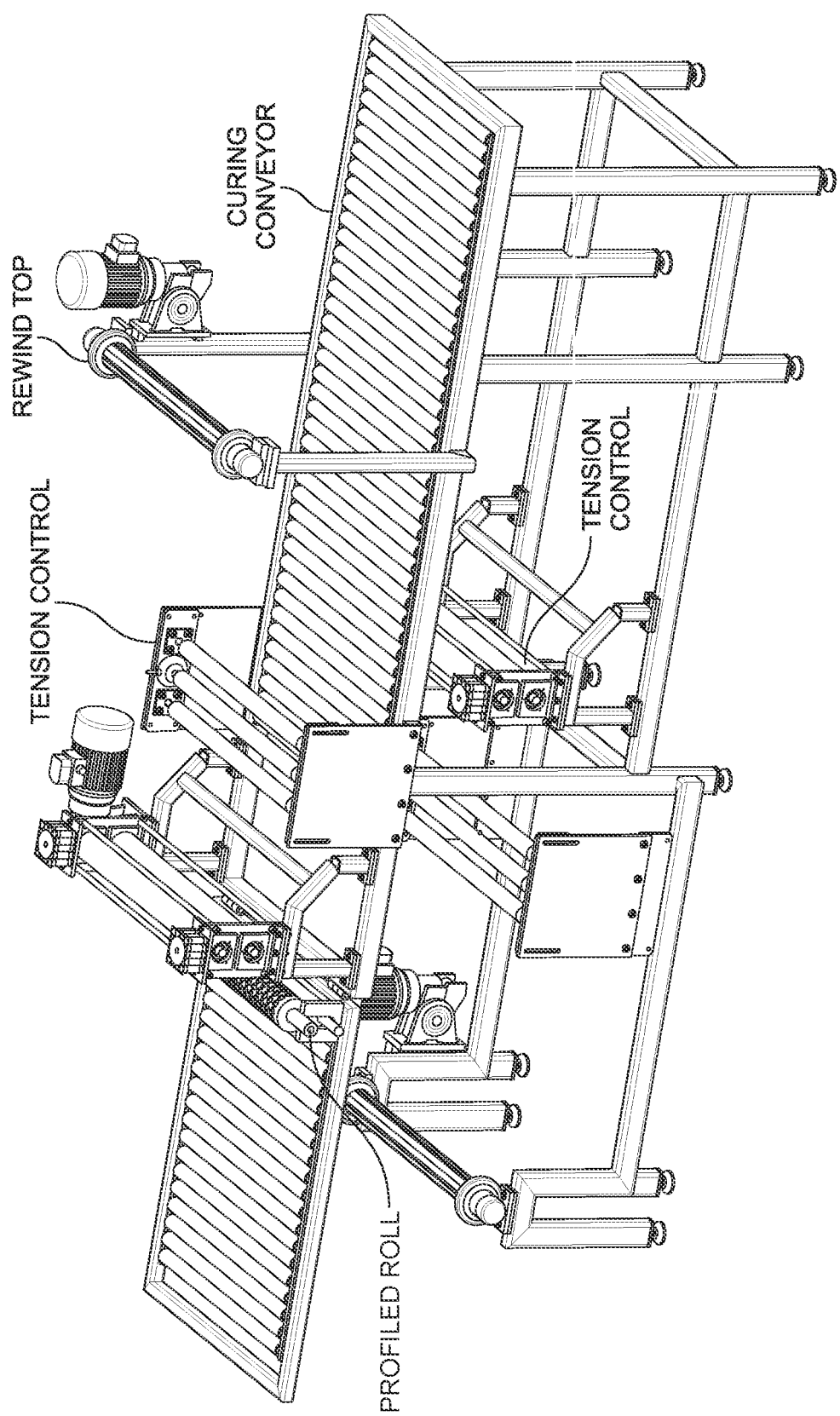

The structure of a suitable honeycomb roller is depicted in FIG. 1A. The positioning of a profiling roller of the present invention on the foam line production assembly is shown in FIG. 1B.

As used herein, the terms "profiling roller", "profiling roll", "profiled roller" and "profiled roll" are synonymous.

In the process of the present invention, a profiling step takes place before the drying step, such as immediately before the drying step.

In some embodiments, all profiling takes place before the drying step. In other embodiments, profiling may also take place after the drying step, or before and after the drying step.

In some embodiments, the profiling step takes place after the curing step, such as immediately after the curing step. In the same or different embodiment, the profiling step occurs after, such as immediately after, the foam has risen to its final size. In this regard, profiling after the curing step or rise time may be advantageous because the foam may not further distort post-profiling.

Preferably, the profiling step takes place after (such as immediately after) the curing step and/or foaming step and/or after the foam has risen to its final size or maximum height, and before (such as immediately before) the drying step. In other words, the profiling step may take place (exactly) between the curing step and the drying step. Accordingly, the profiling step may take place after the entire curing step has taken place, and before any drying has taken place, such as (immediately) before the drying step. In an embodiment, the profiling step takes place after the foam has fully cured and before the drying step. In a related embodiment, the profiling step takes place after the rise time.

Figure 2:
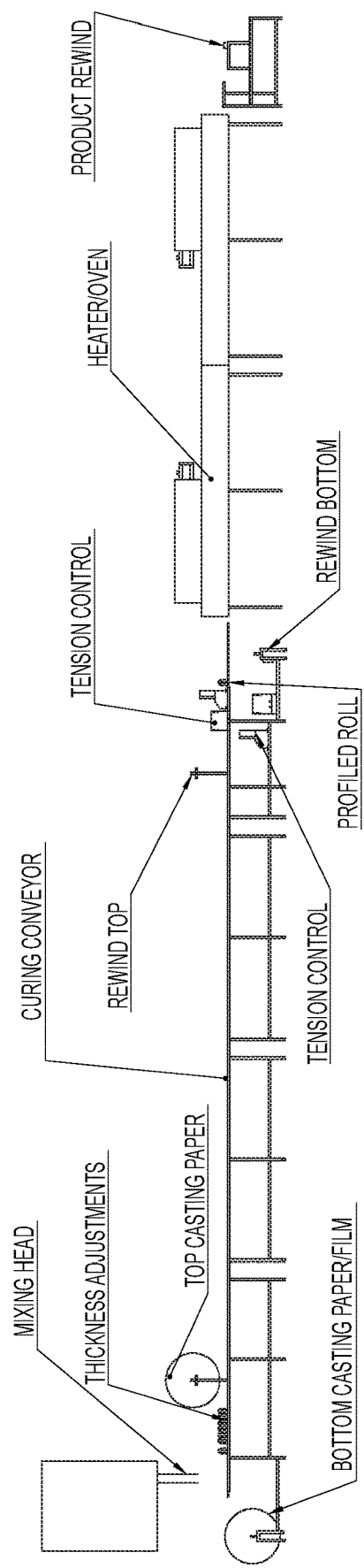
FIG. 2 is an annotated diagram of a foam line production assembly.

As an example, the set-up in FIG. 2 depicts a profiled roll positioned immediately before the drying oven, i.e. exactly between the curing step and the drying step. Whilst there may be a small section of conveyor between the profiling means and drying means, curing is to be considered complete by the time the product is profiled. In FIG. 2, said small section of conveyor functions to deliver the profiled product into the drying tunnel.

Accordingly, the present invention provides a process for producing a profiled absorbent polyurethane foam product, said process comprising the sequential steps of:
a) providing a composition comprising at least one polyurethane prepolymer;
b) simultaneously foaming and curing said polyurethane prepolymer composition;
c) profiling the foamed composition after curing;
d) drying the foamed composition after profiling.

Prior to the present invention, and without wishing to be bound by theory, there was a prejudice in the art that certain foam compositions were unsuitable for profiling before drying had occurred, since it was believed that such compositions comprised too much water to be suitably profiled.

In this regard, some foam line processes in the art teach the contouring of foam prior to "end-of-cure". In such cases, it is inevitable that some drying of the foam will have already occurred before the profiling step.

Accordingly in another aspect the present invention provides a profiled, cured and non-dried (e.g. non-heated) absorbent polyurethane foam product, and in another aspect a pre-dried (e.g. pre-heated), profiled, cured and absorbent polyurethane foam product.

In a related embodiment, the profiling step occurs before any curing takes place.

The profiling step results in a product which has compressed or indented portions in places where the profiling means has come into physical contact with the foam and non-compressed portions (which are raised relative to the compressed/indented portions) in places where the profiling means has not come into contact with the foam.

Accordingly, the terms "raised/indented" and "compressed/non-compressed" are two ways of describing the same features of the invention. The first denotes the relative positioning of the portions of the foam product in relief. The second denotes whether or not the portion in question has been subjected to pressure or flattened by a mechanical means, such as a profiling means, such as a profiling means (e.g. a roller) of the invention. Accordingly, the two sets of terms may be used interchangeably.

Apparatus

The present invention provides an apparatus for producing a profiled absorbent polyurethane foam product, said apparatus comprising curing means, drying means and profiling means; wherein said profiling means are operably located between the curing means and the drying means.

The descriptions of the curing means, drying means and profiling means in relation to other aspects of the present invention are equally applicable to the apparatus of the invention.

The apparatus of the invention may further comprise one or more of the following: a mixing head, foam thickness-adjusting means, one or more pay-off rollers, tension-controlling means, rewind reel.

At the mixing head, the prepolymer composition (e.g. component A)) may be mixed with the aqueous phase (e.g. components B), C) and D)). The mixing head may rotate at any rpm, and mixing may take place at a temperature elevated from room temperature. The foam thickness adjusting means functions to adjust the final thickness of the mixed composition prior to curing The pay-off rollers are suitable for layering the composition onto or between one or more films, papers or laminates, in particular release papers. Suitable component of such films, papers and laminates include PTFE and charcoal.

The polyurethane prepolymer composition of the present invention may be provided onto release paper or layered between one or more release papers. The release paper may be paper coated with a high temperature resistant polymer. Preferably, the release paper is speciality imaging paper, for example that from Felix Schoeller.

The tension-controlling means function to control the tension in e.g. the release paper(s). The rewind reel is where the final product exits the production line.

FIG. 2 depicts an annotated diagram of a foam line assembly apparatus according to the present invention. In one embodiment, the present invention provides an apparatus as described with reference to FIG. 2.

Additional Processing

Additional processing of the absorbent product of the present invention may be in the form of a second profiling step, for example after the drying step.

The additional processing may also comprise providing the polyurethane foam prepolymer composition as a layer onto or between one or more films or alginate-based layers, and/or providing the absorbent product with one or more skin/wound-facing or non-skin/wound-facing adhesive layers.

Films or alginate-based layers may be provided on the top of bottom of the absorbent product of the invention. Preferably, the polyurethane prepolymer composition is provided or bonded between one film layer and one alginate-based layer. Preferably, no adhesive is used in such layering or bonding.

Suitable films include those from Covestro under the name AQUACEL®. Suitable alginate-based layers include those from Speciality Fibres and Materials Ltd (SFM).

Accordingly, the present invention provides an absorbent product comprising a polyurethane layer, a film layer and an alginate-based layer. Preferably the polyurethane layer is layered between the film layer and the alginate layer. Preferably the polyurethane is aliphatic polyurethane such as hydrophilic aliphatic polyurethane. Preferably the product does not comprise any adhesive, either between the layers or on the external surfaces of the product.

The additional processing may also comprise providing the polyurethane foam as a first layer laminated to or juxtaposed with an additional (e.g. a different) polyurethane foam as a second layer. The polyurethane foams of the first and second layers may have different properties. For example, the second layer may have different absorbency, fluid retention and/or thermoformability in comparison to the first layer. The properties of the two polyurethanes may thus be advantageously combined in the foam product of the invention. Suitable additional polyurethane layers are described herein.

Accordingly, the present invention provides an absorbent aliphatic polyurethane foam product having at least one profiled surface comprising a first polyurethane layer laminated to or juxtaposed with a second polyurethane layer, wherein the second layer has different properties to the first layer. In an embodiment, the second layer is thermoformable. In an embodiment, the second layer has different absorbency, such as higher or lower absorbency and/or lower fluid retention than the first layer. The first layer may be a foam manufactured from BAYMEDIX® FP505 prepolymer and the second layer may be a foam manufactured from BAYMEDIX® FD103 prepolymer.

Examples

The present invention is further described by way of the following non-limiting examples:

Example 1—Capillary Action

A dimpled aliphatic polyurethane absorbent product as depicted in FIG. 4A was challenged with droplets of synthetic blood at the positions marked with "+" (see FIG. 4B).

The synthetic blood was effectively absorbed and distributed away from the original challenge sites into the indentations or "valleys") i.e. indented or compressed regions in the product (FIG. 4B), to then be stored in the raised "hills" or non-compressed regions. This demonstrates superior capillary action and clearing of fluid from a theoretical wound area.

Example 2—Comparative Example

An absorbent product of the present invention (sometimes referred to herein as SENTIENT®) was tested alongside four competitor marketed products (ACTIVHEAL®, ALLEVYN®, BIATAIN® and MEPILEX®) for the properties of absorption, retention, thickness increase and speed of absorption.

Example 2A—Absorption

Each weighed dressing was placed into a container containing an excess solution of 0.9 wt. % saline at 36° C. This was then put into an incubator at 35° C. for 30 minutes. After this time each dressing was suspended vertically for 30 seconds and then weighed.

Figure 7:
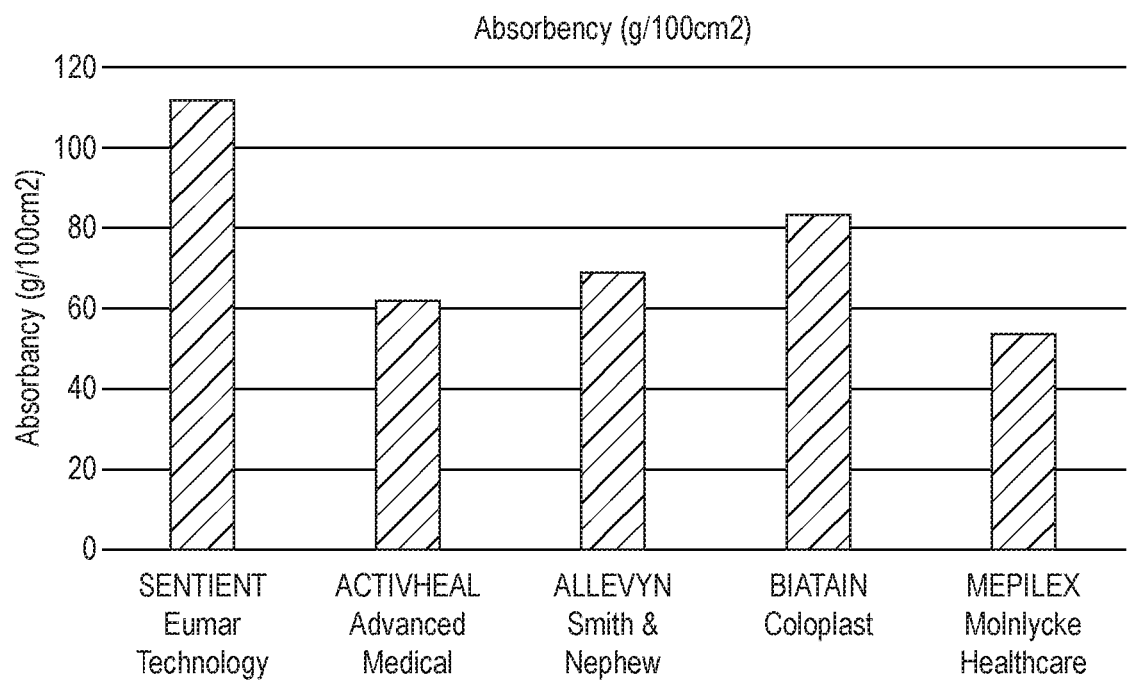
FIG. 7 is a comparative bar chart of the absorbency (g/100 cm$^2$) of various foam products.
Figure 8:
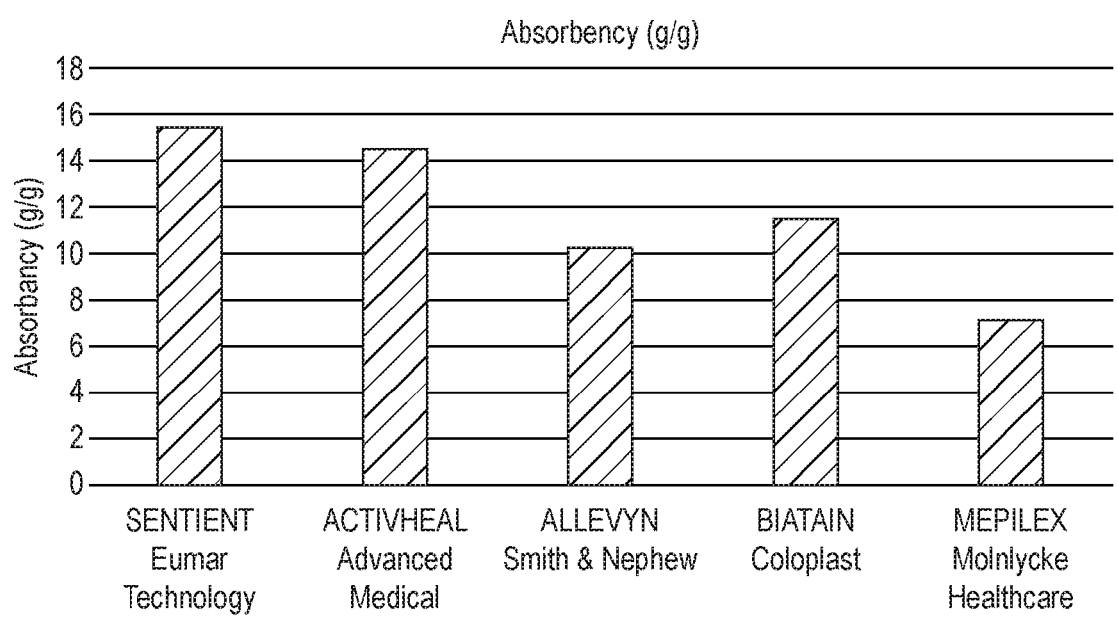
FIG. 8 is a comparative bar chart of the absorbency (g/g) of various foam products.

The results are shown in FIG. 7 (g/100 cm$^2$) and FIG. 8 (g/g). The product of the present invention demonstrated the best absorption capability.

Example 2B—Retention

Following the test in Example 1, the dressings were uniformly compressed with a 4 kg mass for 30 seconds then reweighed. Lastly each dressing was subjectively compressed by hand and finally reweighed.

Figure 9:
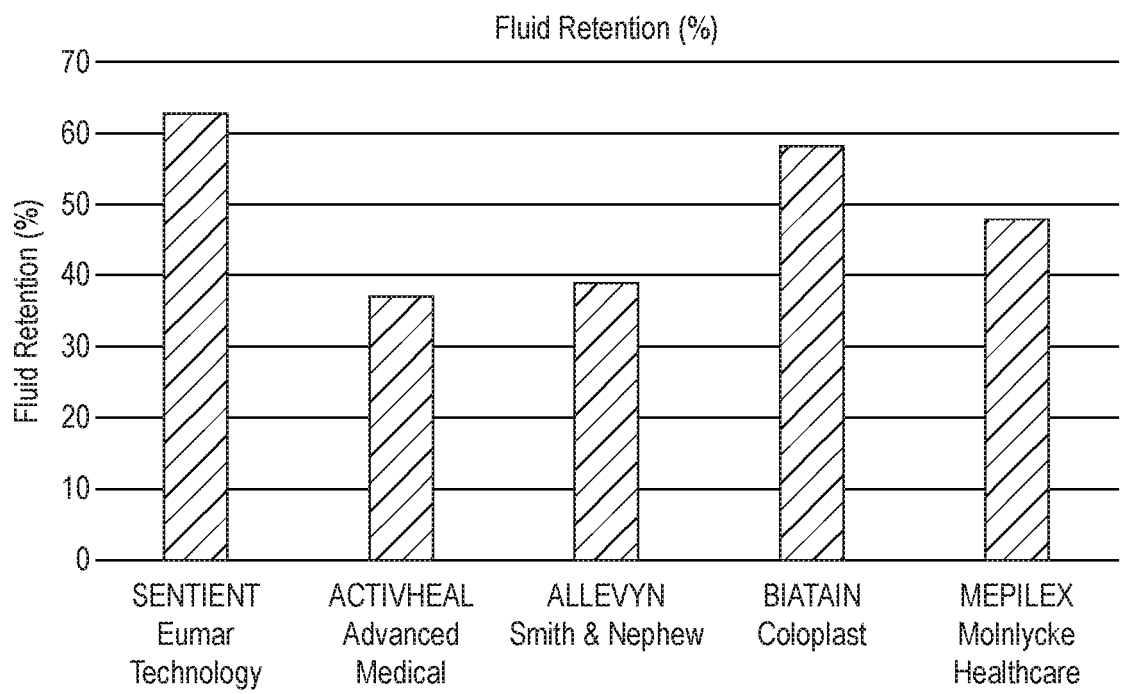
FIG. 9 is a comparative bar chart of the fluid retention (%) of various foam products.

The results are shown in FIG. 9 (% fluid retention). The product of the present invention demonstrated the best fluid retention capability.

Example 2C—Thickness Increase

The thickness of each dressing was measured before and after the absorption test in Example 2A. The difference was then used to create a percentage increase.

Figure 10:
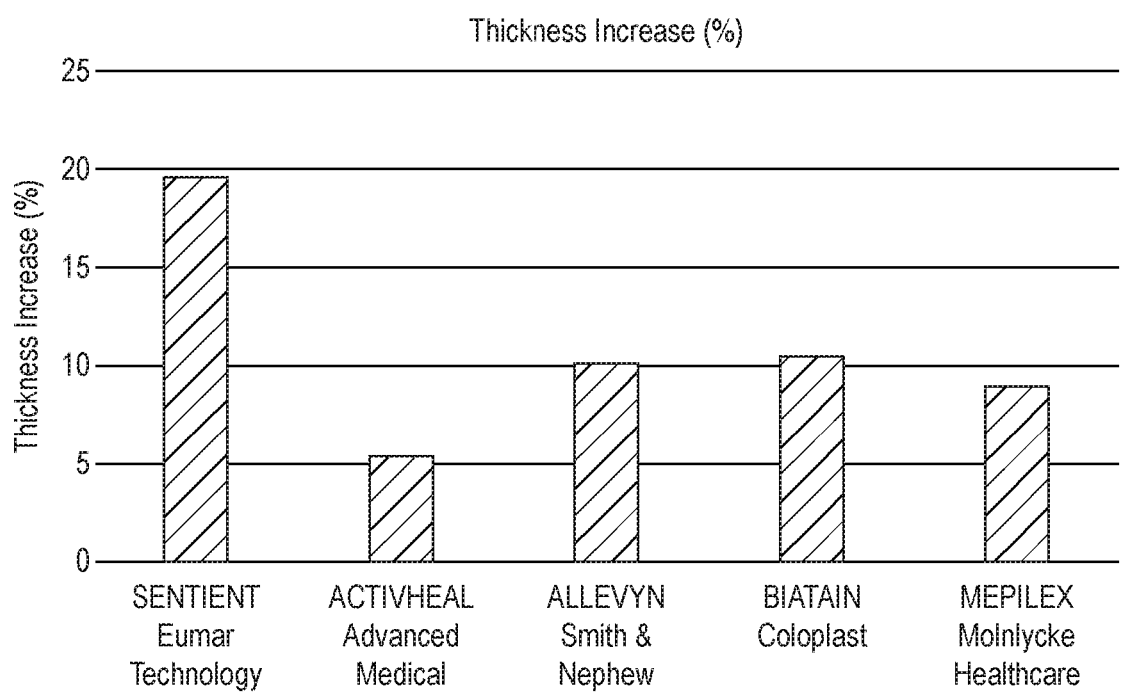
FIG. 10 is a comparative bar chart of the thickness increase (%) of various foam products.

The results are shown in FIG. 10. The product of the present invention demonstrated the greatest increase in thickness.

Example 2D—Speed of Absorption

Figure 11:
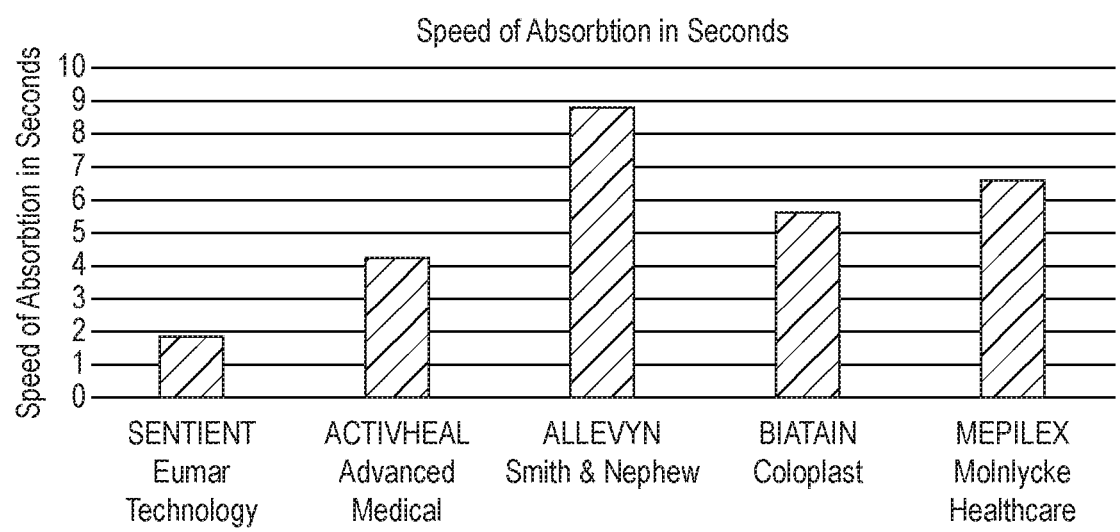
FIG. 11 is a comparative bar chart of the speed of absorption (s) of various foam products.

Using a syringe having 2 mm aperture, a saline solution was dropped onto the dressing. The time from contact to full absorption into the dressing was timed. This process was repeated 5 times to obtain an average. It was this average that was used in the results shown in FIG. 11. The product of the present invention demonstrated the fastest absorption time.

Example 3—Comparison of Compressed and Non-Compressed Portions

An absorbent product of the present invention having a "flower" shaped profile design (shown in FIG. 20) was tested for the properties of absorption, fluid retention, thickness increase and speed of absorption. The compressed portion (i.e. the flower itself) and the non-compressed portion (the region between the flower and the product edge) were tested separately and the results compared.

Example 3A—Absorption

The dressing was separated into its compressed and non-compressed portions by cutting the dressing. Each portion was weighed was placed into a container containing an excess solution of 0.9 wt. % saline at 36° C. This was then put into an incubator at 35° C. for 30 minutes. After this time each portion was suspended vertically for 30 seconds and then weighed.

Figure 15:
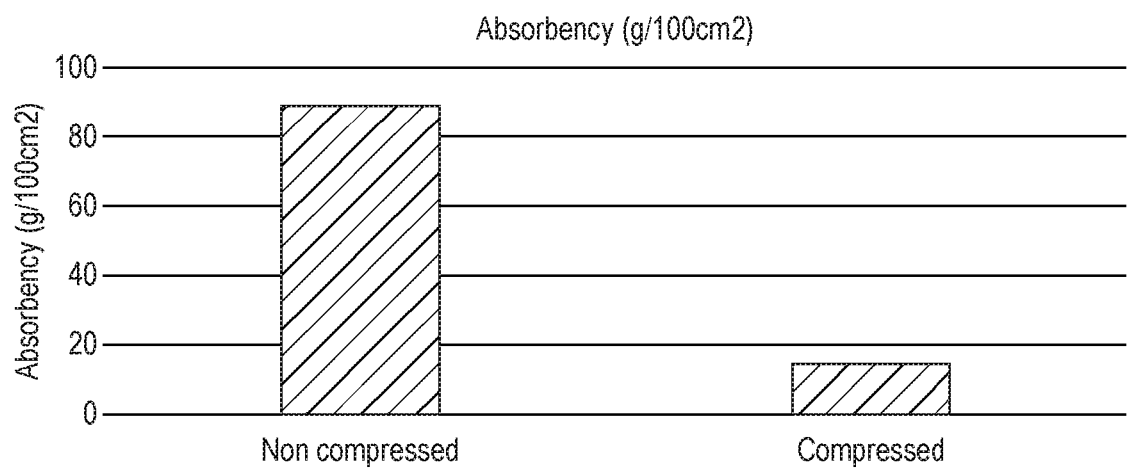
FIG. 15 is a comparative bar chart of the absorbency (g/100 cm$^2$) of the compressed and non-compressed portions of a flower-shaped dressing of the invention.
Figure 16:
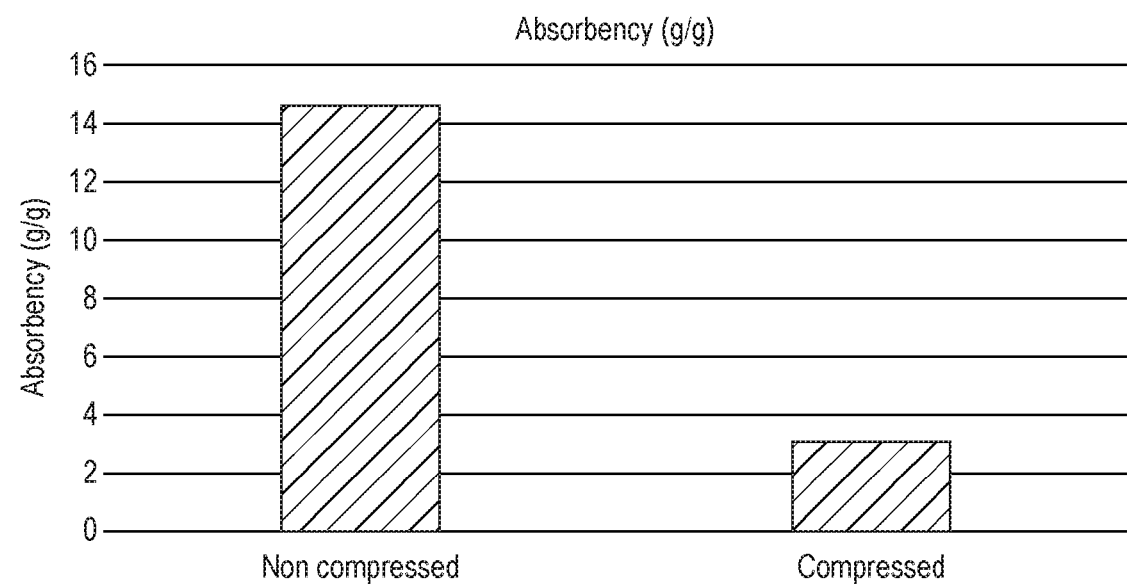
FIG. 16 is a comparative bar chart of the absorbency (g/g) of the compressed and non-compressed portions of a flower-shaped dressing of the invention.

The results are shown in FIG. 15 (g/100 cm$^2$) and FIG. 16 (g/g). The compressed portion exhibited less absorption capability than the non-compressed portion.

Example 3B—Thickness Increase

Figure 20:
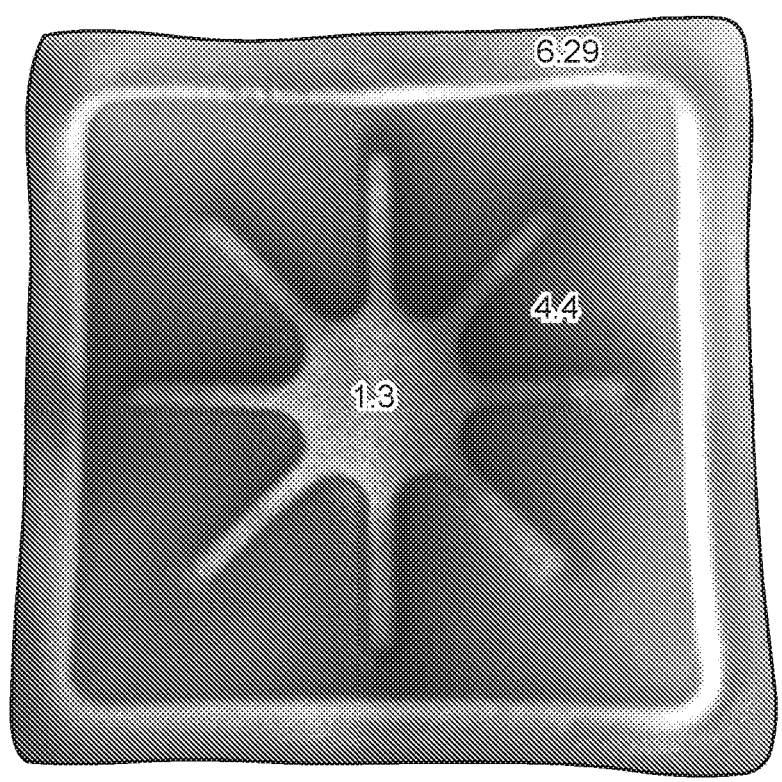
FIG. 20 is a photographic image of a flower shaped dressing which was used to carry out the tests in FIGS. 15-19. The dressing has a thickness of 1.3 mm at the compressed portion and 4.4 mm at the non-compressed portion, prior to testing. The weight of the dressing was 6.29 g, prior to testing.
Figure 21:
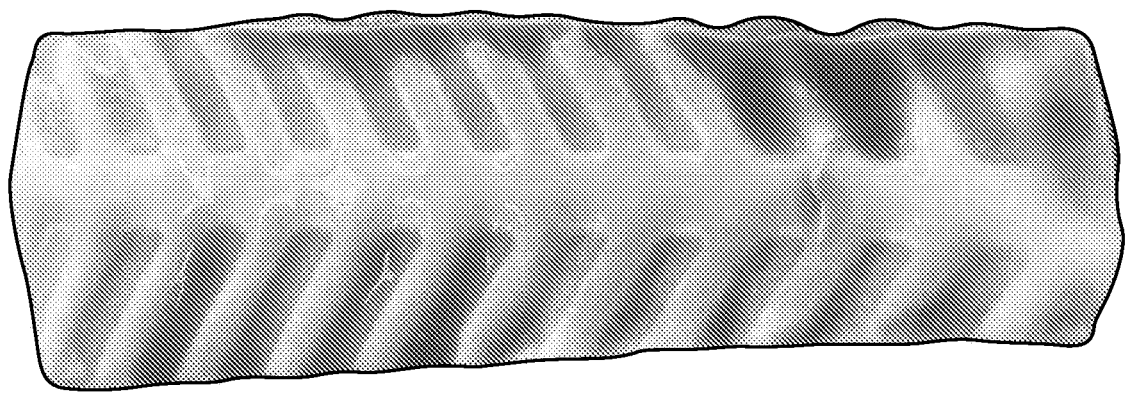
FIG. 21 is a representative photographic image of the underside (i.e. non-profiled side) of a herringbone profiled dressing of the present invention, which has been challenged with synthetic blood.

The thickness of each portion was measured before and after the absorption test in Example 3B. The thickness in mm of each portion before absorption test is shown in FIG. 20 (1.3 mm for the compressed portion and 4.4 mm for the non-compressed portion). The difference in thickness before and after the test was then used to create a percentage increase.

Figure 17:
FIG. 17 is a comparative bar chart of the thickness increase (%) of the compressed and non-compressed portions of a flower-shaped dressing of the invention.

The results are shown in FIG. 17. The compressed portion exhibited a reduced thickness increase after absorption test when compared to the non-compressed portion.

Example 3C—Speed of Absorption

Figure 18:
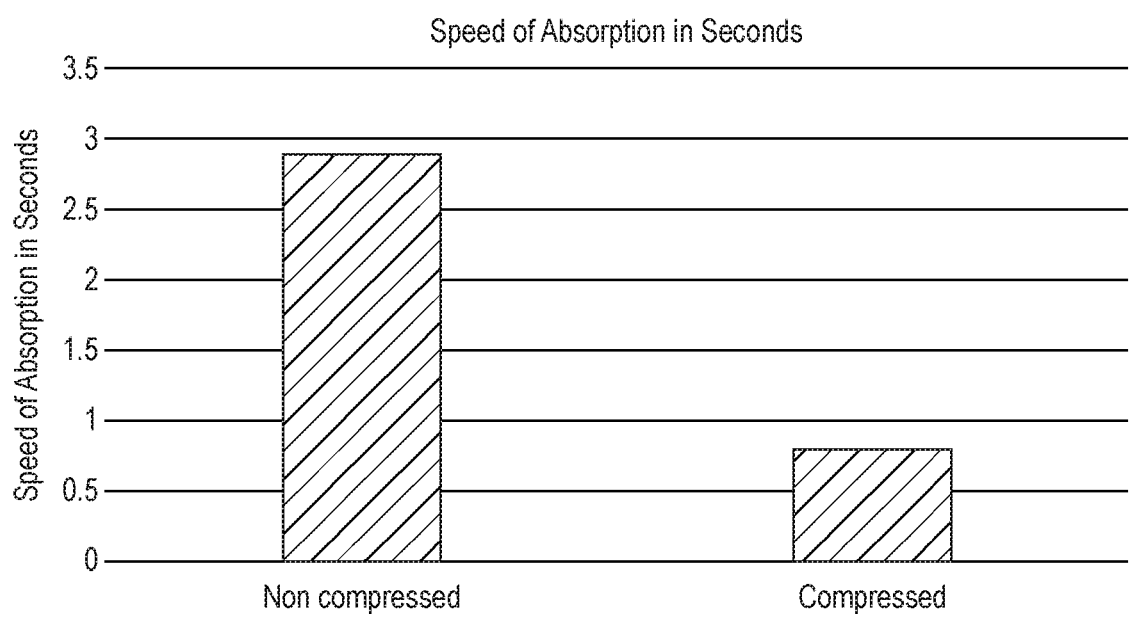
FIG. 18 is a comparative bar chart of the speed of absorption (s) of the compressed and non-compressed portions of a flower-shaped dressing of the invention.

Using a syringe having 2 mm aperture, a saline solution was dropped onto each portion. The time from contact to full absorption into the dressing portion was timed. This process was repeated 5 times to obtain an average. It was this average that was used in the results shown in FIG. 18. The compressed portion demonstrated a faster absorption time than the non-compressed portion.

Example 3D—Retention

Following the test in Example 3A, the excised portions were uniformly compressed with a 4 kg mass for 30 seconds then reweighed. Lastly each portion was subjectively compressed by hand and finally reweighed.

Figure 19:
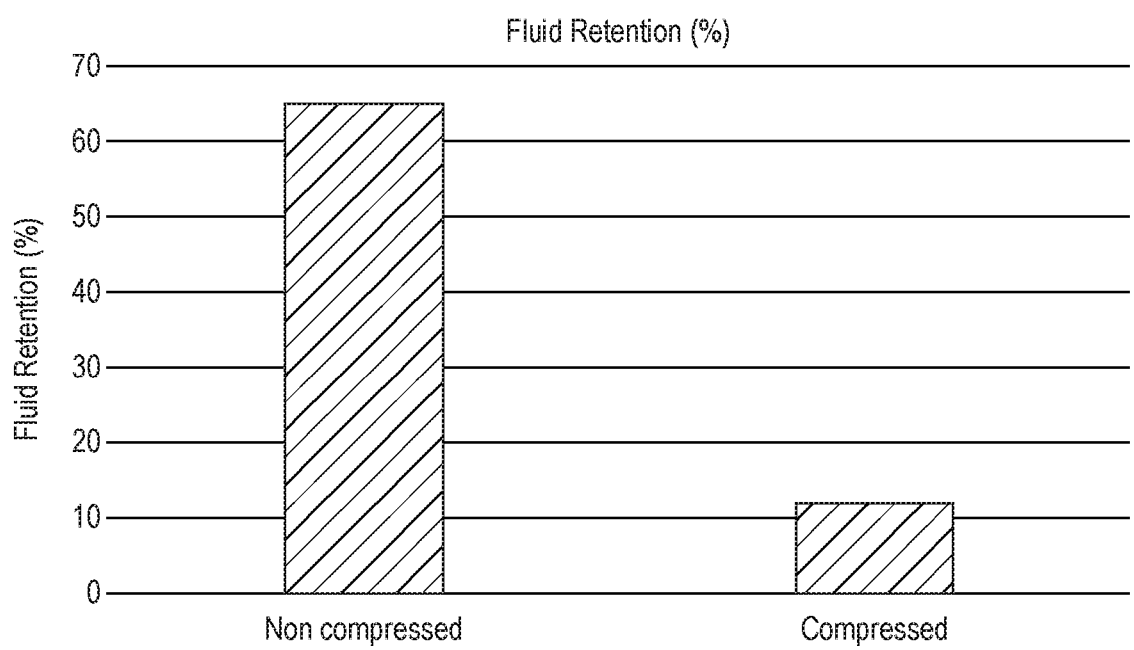
FIG. 19 is a comparative bar chart of the fluid retention (%) of the compressed and non-compressed portions of a flower-shaped dressing of the invention.

The results are shown in FIG. 19 (% fluid retention). The compressed portion exhibited lower fluid retention capability than the non-compressed portion.

The methods in Examples 3A-3D were repeated for a 'dimpled' dressing of the present invention and the same or very similar results were obtained.

All documents cited in the present specification are hereby incorporated by reference in their entirety.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. The terms or definitions used herein are provided solely to aid in the understanding of the invention.

Reference throughout this specification to "one embodiment" or "an embodiment" means that a particular feature, structure or characteristic described in connection with the embodiment is included in at least one embodiment of the present invention. Thus, appearance of the phrases "in one embodiment" or "in an embodiment" in various places throughout this specification are not necessarily all referring to the same embodiment, but may do so. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

The invention also relates to the aspects defined in the following numbered paragraphs:

1. A process for producing a profiled absorbent polyurethane foam product, said process comprising the steps of:
   a) providing and/or preparing a foamed polyurethane prepolymer composition;
   b) curing the foamed composition;
   c) profiling the foamed composition;
   d) drying the foamed composition
   wherein said profiling step (c) occurs before said drying step (d).
2. Process according to paragraph 1, wherein the polyurethane foam is aliphatic polyurethane foam.
3. Process according to paragraph 1 or paragraph 2, wherein the polyurethane foam is hydrophilic aliphatic polyurethane foam.
4. Process according to any preceding paragraph, wherein the polyurethane foam is prepared by a method comprising reacting an aliphatic isocyanate-based prepolymer with water and surfactant in the presence of a catalyst.
5. Process according to any preceding paragraph, wherein step (c) is carried out using a profiling roller.
6. Process according to any preceding paragraph, further comprising the steps of:
   e) providing a composition comprising at least one polyurethane prepolymer;
   f) foaming the composition to form said foamed polyurethane prepolymer composition in step a).
7. Process according to paragraph 6, wherein the composition in step (e) is:
   (i) provided onto release paper or layered between one or more release papers; and/or
   (ii) provided as a layer between a film layer and an alginate-based layer, preferably in the absence of an adhesive.
8. Process according to any preceding paragraph, wherein all profiling takes place before drying step (d).
9. Process according to any preceding paragraphs, wherein the profiling step (c) takes place after the curing step (b) and before the drying step (d).
10. An absorbent aliphatic polyurethane foam product obtainable by a process according to any one of the preceding paragraphs.
11. An absorbent aliphatic polyurethane foam product obtained by a process according to any one of the preceding paragraphs.
12. An absorbent aliphatic polyurethane foam product having at least one profiled surface.
13. Absorbent product of paragraph 12, wherein the profiled surface comprises a bevelled edge, preferably wherein the bevel is comprised within the outermost 0.2 cm of the rim of the product, preferably wherein the density of the foam is between about 80 to about 500 kg/m$^3$.
14. Absorbent product of paragraph 12 or paragraph 13, wherein the profiled surface comprises one or more raised portions.
15. Absorbent product of any one of paragraphs 12 to 14, wherein the profiled surface comprises a pattern of connected or interconnected indentations formed into said surface to provide one or more raised portions.
16. Absorbent product of paragraph 15, wherein said pattern of connected indentations are non-linear, and progress in at least three main directions, preferably at an angled propagation, even more preferably in the form of a honeycomb pattern.
17. Absorbent product of any one of paragraphs 14 to 16, wherein the raised portions are of essentially circular or hexagonal cross-section.
18. Absorbent product of any one of paragraphs 12 to 17, wherein the profiled surface comprises a pattern of connected or interconnected raised portions formed into said surface, preferably comprising a central elongate raised portion extending substantially from one edge of the product to the (diametrically) opposite or substantially parallel edge, and a plurality of additional elongate raised portions extending from the central raised portion, preferably substantially to one or more edges of the product.
19. Absorbent product of any one of paragraphs 12 to 18, wherein the profiled surface comprises V-shaped or herringbone profiling.
20. Absorbent product of paragraph of any one of paragraphs 12 to 19, wherein the profiled surface comprises a plurality of elongate raised portions radiating from a raised portion positioned essentially centrally on said surface.
21. Absorbent product of any one of paragraphs 12 to 20 comprising a polyurethane layer, a film layer and an alginate-based layer.
22. An absorbent aliphatic polyurethane foam product having one or more of the following properties:
   (i) density of less than about 100 kg/1n$^3$;
   (ii) absorbency of greater than about 85 g/100 cm$^2$;
   (iii) absorbency of greater than about 14.5 g/g;
   (iv) fluid retention of greater than about 58%;
   (v) thickness increase after absorption test of greater than about 11%;

(vi) speed of absorption of fluid droplet of less than about 4.3 seconds.

23. A profiled, cured and non-dried absorbent polyurethane foam product.

24. A pre-dried, profiled, cured and absorbent polyurethane foam product.

25. The absorbent product of any one of paragraphs 10 to 24, wherein said absorbent product is a dressing, wound dressing, pad, lactation pad, heel pad, incontinence pad, sanitary pad, nappy (diaper), sanitary product, hygiene product, feminine hygiene product or maternity towel.

26. An apparatus for producing a profiled absorbent polyurethane foam product, said apparatus comprising:
   a) curing means;
   b) drying means;
   c) profiling means;
   wherein said profiling means (c) are operably located between the curing means and the drying means.

27. Apparatus according to paragraph 26, wherein the profiling means comprises a profiling roller.

28. Apparatus according to paragraph 26 or paragraph 27, further comprising one or more of the following:
   d) a mixing head;
   e) foam thickness-adjusting means;
   f) one or more pay-off rollers;
   g) tension-controlling means;
   h) rewind reel.

29. Process substantially as described herein and with reference to the Figures.

30. Absorbent product substantially as described herein and with reference to the Figures.

31. Apparatus substantially as described herein and with reference to the Figures.

What is claimed:

1. An absorbent aliphatic polyurethane foam product having at least one profiled surface, wherein the profiled surface comprises:
   one or more indented, compressed portions and one or more raised, non-compressed portions;
      wherein, the one or more raised, non-compressed portions have a lower density than the one or more indented, compressed portions, wherein the one or more raised, non-compressed portions have a density of 100 to 140 kg/m$^3$ and the one or more indented, compressed portions have a density of 140 to 180 kg/m$^3$;
      wherein, the one or more raised, non-compressed portions have a greater absorbency of fluid than the one or more indented, compressed portions; wherein the one or more raised, non-compressed portions have an absorbency of fluid of greater than about 40 g/100 cm$^2$;
      wherein, the one or more indented, compressed portions have a faster speed of absorption of a fluid droplet when compared to the one or more raised, non-compressed portions;
      wherein the indented, compressed portions have a lower fluid retention than the raised, non-compressed portions;
   wherein, the one or more raised, non-compressed portions are reservoirs for absorbed fluid and the one or more indented, compressed portions have capillary motor action of fluid between neighbouring regions of the one or more raised, non-compressed portion, or between neighbouring raised, non-compressed portions;
   and wherein, the absorbent aliphatic polyurethane foam product has a more even distribution of the absorbed fluid around the foam product as compared to an equivalent non-profiled product.

2. The absorbent aliphatic polyurethane foam product of claim 1, wherein:
   the indented, compressed portions have a reduced thickness increase after absorption test when compared to the raised, non-compressed portions.

3. The absorbent aliphatic polyurethane foam product of claim 1, wherein the raised, non-compressed portions have one or more of the following properties:
   (i) fluid retention of greater than about 50%;
   (ii) thickness increase after absorption test of greater than about 40%;
   (iii) speed of absorption of fluid droplet of about 1 to about 4.3 seconds;
and/or wherein the indented, compressed portions have one or more of the following properties:
   (i) absorbency of less than about 40 g/100 cm2;
   (ii) absorbency of less than about 5 g/g;
   (iii) fluid retention of less than about 50%;
   (iv) thickness increase after absorption test of less than about 40%;
   (v) speed of absorption of fluid droplet of less than about 1 second.

4. The absorbent aliphatic polyurethane foam product of claim 1, wherein the profiled surface comprises a pattern of connected or interconnected indented, compressed portions formed into said surface to provide the one or more raised, non-compressed portions, optionally, wherein said pattern of connected indentations are non-linear, and progress in at least three main directions in the form of a honeycomb pattern.

5. The absorbent aliphatic polyurethane foam product of claim 1, wherein the profiled surface comprises a pattern of connected or interconnected raised, non-compressed portions formed into said surface, optionally, comprising a central elongate raised, non-compressed portion extending substantially from one edge of the product to the diametrically opposite or substantially parallel edge, and a plurality of additional elongate raised, non-compressed portions extending from the central raised, non-compressed portion.

6. The absorbent aliphatic polyurethane foam product of claim 1, wherein the profiled surface comprises a plurality of elongate indented, compressed portions radiating from an indented, compressed portion positioned essentially centrally on said surface, optionally wherein the central indented, compressed portion is essentially circular.

7. The absorbent aliphatic polyurethane foam product of claim 1, further comprising one or more additives/active ingredients, optionally, wherein the one or more additives/active ingredients comprise one or more of the following:
   i) chlorhexidine;
   ii) silver or salts thereof; or
   iii) sodium chloride.

8. The absorbent aliphatic polyurethane foam product of claim 1, further comprising a film layer and/or an alginate-based layer.

9. The absorbent aliphatic polyurethane foam product of claim 1, comprising a first polyurethane layer laminated to or juxtaposed with a second polyurethane layer, wherein the second layer has different properties to the first layer, optionally wherein the second layer has a higher or lower absorbency and/or lower fluid retention than the first layer.

10. The absorbent aliphatic polyurethane foam product of claim 1, comprising a layer of non-woven material.

11. The absorbent aliphatic polyurethane foam product of claim 1, wherein the product is shaped to conform to the contours of a body part, optionally a breast or heel.

12. The absorbent aliphatic polyurethane foam product of claim 1, wherein said absorbent product is a dressing, wound dressing, pad, breast pad, lactation pad, heel pad, bed sore prevention pad, incontinence pad, sanitary pad, diaper, sanitary product, hygiene product, feminine hygiene product or maternity towel.

13. The absorbent aliphatic polyurethane foam product of claim 1, wherein the raised, non-compressed portions are of essentially circular or hexagonal cross-section.

14. The absorbent aliphatic polyurethane foam product of claim 1, wherein the profiled surface comprises a pattern of connected or interconnected indented, compressed portions formed into said surface, optionally comprising a central elongate indented, compressed portion extending substantially from one edge of the product to the diametrically opposite or substantially parallel edge, and a plurality of additional elongate indented, compressed portions extending from the central indented, compressed portion.

15. The absorbent aliphatic polyurethane foam product of claim 1, wherein the profiled surface comprises V-shaped or herringbone profiling.

16. The absorbent aliphatic polyurethane foam product of claim 1, comprising a single polyurethane layer.

* * * * *